(12) United States Patent
Chomas et al.

(10) Patent No.: US 10,548,659 B2
(45) Date of Patent: Feb. 4, 2020

(54) HIGH PRESSURE PRE-BURST FOR IMPROVED FLUID DELIVERY

(75) Inventors: James E. Chomas, Boulder, CO (US); Mark E. Deem, Mountain View, CA (US); Hanson S. Gifford, Woodside, CA (US); Douglas S. Sutton, Pacifica, CA (US)

(73) Assignee: ULTHERA, INC., Mesa, AZ (US)

( * ) Notice: Subject to any disclaimer, the term of this patent is extended or adjusted under 35 U.S.C. 154(b) by 1447 days.

(21) Appl. No.: 12/555,746

(22) Filed: Sep. 8, 2009

(65) Prior Publication Data
US 2009/0326439 A1 Dec. 31, 2009

Related U.S. Application Data

(63) Continuation-in-part of application No. 11/515,634, filed on Sep. 5, 2006, now abandoned, and a
(Continued)

(51) Int. Cl.
*A61B 18/14* (2006.01)
*A61B 18/00* (2006.01)
*A61N 7/00* (2006.01)

(52) U.S. Cl.
CPC .. *A61B 18/1477* (2013.01); *A61B 2018/0016* (2013.01); *A61B 2018/00452* (2013.01);
(Continued)

(58) Field of Classification Search
CPC ........ A61H 2201/0207; A61H 2201/10; A61H 2201/105; A61H 2207/00; A61H 23/0245;
(Continued)

(56) References Cited

U.S. PATENT DOCUMENTS

| | | |
|---|---|---|
| 2,370,529 A | 2/1945 | Fuller |
| 2,490,409 A | 12/1949 | Brown |

(Continued)

FOREIGN PATENT DOCUMENTS

| | | |
|---|---|---|
| CA | 1232837 | 2/1988 |
| CA | 1239092 | 7/1988 |

(Continued)

OTHER PUBLICATIONS

Albrecht, T., et al., Guidelines for the Use of Contrast Agents in Ultrasound, Ultraschall in Med 2004, Jan. 2004, pp. 249-256, vol. 25.
(Continued)

*Primary Examiner* — Michael F Peffley
*Assistant Examiner* — Samantha M Good
(74) *Attorney, Agent, or Firm* — Knobbe, Martens, Olson & Bear LLP

(57) ABSTRACT

A needle with multiple injection ports is used in connection with a high-pressure injection system to infuse a treatment solution into a treatment area below the dermis of the skin. The needle has multiple tines that extend outwardly from the injection ports while inside the treatment area to disrupt tissue in the treatment area and to create multiple pathways of infusion. The tines are withdrawn and the needle is partially withdrawn, and solution is injected from the needle into the treatment area at high pressure to infuse the tissue within the treatment area. The burst, infusion, and a treatment such as an energy or third solution may be interleaved and repeated multiple times.

16 Claims, 8 Drawing Sheets

Related U.S. Application Data continuation-in-part of application No. 11/334,794, filed on Jan. 7, 2006, now Pat. No. 7,588,547.

(52) U.S. Cl.
CPC . *A61B 2018/143* (2013.01); *A61B 2018/1432* (2013.01); *A61B 2218/002* (2013.01); *A61H 2207/00* (2013.01); *A61N 2007/0008* (2013.01)

(58) Field of Classification Search
CPC .. A61B 2018/0016; A61B 2018/00452; A61B 2018/1425; A61B 2018/143; A61B 2018/1432; A61B 18/1402; A61B 18/1477; A61B 2218/002; A61B 2218/007; A61M 5/32; A61N 1/327; A61N 2007/0008; A61N 2005/0661
USPC .......................................... 606/41; 604/19–22
See application file for complete search history.

(56) References Cited

U.S. PATENT DOCUMENTS

| | | |
|---|---|---|
| 2,738,172 A | 3/1956 | Spiess et al. |
| 2,945,496 A | 7/1960 | Fosdal |
| 2,961,382 A | 11/1960 | Singher et al. |
| 3,129,944 A | 4/1964 | Amos et al. |
| 3,324,854 A | 6/1967 | Weese |
| 3,590,808 A | 7/1971 | Muller |
| 3,735,336 A | 3/1973 | Long |
| 3,964,482 A | 6/1976 | Gerstel et al. |
| 3,991,763 A | 11/1976 | Genese |
| 4,150,669 A | 4/1979 | Latorre |
| 4,188,952 A | 2/1980 | Loschilov et al. |
| 4,211,949 A | 7/1980 | Brisken et al. |
| 4,212,206 A | 7/1980 | Hartemann et al. |
| 4,231,368 A | 11/1980 | Becker et al. |
| 4,248,231 A | 2/1981 | Herczog et al. |
| 4,249,923 A | 2/1981 | Walda |
| 4,276,885 A | 7/1981 | Tickner et al. |
| 4,299,219 A | 11/1981 | Norris, Jr. |
| 4,309,989 A | 1/1982 | Fahim |
| 4,373,458 A | 2/1983 | Dorosz et al. |
| 4,382,441 A | 5/1983 | Svedman |
| 4,466,442 A | 8/1984 | Hilman et al. |
| 4,497,325 A | 2/1985 | Wedel |
| 4,536,180 A | 8/1985 | Johnson |
| 4,549,533 A | 10/1985 | Cain |
| 4,608,043 A | 8/1986 | Larkin |
| 4,641,652 A | 2/1987 | Hutterer et al. |
| 4,646,754 A | 3/1987 | Seale |
| 4,657,756 A | 4/1987 | Rasor et al. |
| 4,673,387 A | 6/1987 | Phillips et al. |
| 4,681,119 A | 7/1987 | Rasor et al. |
| 4,684,479 A | 8/1987 | D'Arrigo |
| 4,688,570 A | 8/1987 | Kramer et al. |
| 4,689,986 A | 9/1987 | Carson et al. |
| 4,718,433 A | 1/1988 | Feinstein |
| 4,720,075 A | 1/1988 | Peterson et al. |
| 4,751,921 A | 6/1988 | Park |
| 4,762,915 A | 8/1988 | Kung et al. |
| 4,774,958 A | 10/1988 | Feinstein |
| 4,796,624 A | 1/1989 | Trott et al. |
| 4,797,285 A | 1/1989 | Barenholz et al. |
| 4,815,462 A | 3/1989 | Clark |
| 4,844,080 A | 7/1989 | Frass et al. |
| 4,844,470 A | 7/1989 | Hammon et al. |
| 4,844,882 A | 7/1989 | Widder et al. |
| 4,886,491 A | 12/1989 | Parisi et al. |
| 4,900,311 A | 2/1990 | Stern et al. |
| 4,900,540 A | 2/1990 | Ryan et al. |
| 4,919,986 A | 4/1990 | Lay et al. |
| 4,920,954 A | 5/1990 | Alliger et al. |
| 4,936,281 A | 6/1990 | Stasz |
| 4,936,303 A | 6/1990 | Detwiler et al. |
| 4,957,656 A | 9/1990 | Cerny et al. |
| 5,000,172 A | 3/1991 | Ward |
| 5,022,414 A | 6/1991 | Muller |
| 5,040,537 A | 8/1991 | Katakura |
| 5,050,537 A | 9/1991 | Katakura |
| 5,069,664 A | 12/1991 | Guess et al. |
| 5,083,568 A | 1/1992 | Shimazaki et al. |
| 5,088,499 A | 2/1992 | Unger |
| 5,100,390 A | 3/1992 | Lubeck et al. |
| 5,131,600 A | 7/1992 | Klimpel et al. |
| 5,143,063 A | 9/1992 | Fellner |
| 5,149,319 A | 9/1992 | Unger |
| 5,158,071 A | 10/1992 | Umemura et al. |
| 5,170,604 A | 12/1992 | Hedly |
| 5,178,433 A | 1/1993 | Wagner |
| 5,203,785 A | 4/1993 | Slater |
| 5,209,720 A | 5/1993 | Unger |
| 5,215,104 A | 6/1993 | Steinert |
| 5,215,680 A | 6/1993 | D'Arrigo |
| 5,216,130 A | 6/1993 | Line et al. |
| 5,219,401 A | 6/1993 | Cathignol et al. |
| 5,261,922 A | 11/1993 | Hood |
| 5,308,334 A | 5/1994 | Sancoff |
| 5,310,540 A | 5/1994 | Giddey et al. |
| 5,312,364 A | 5/1994 | Jacobs |
| 5,315,998 A | 5/1994 | Tachibana et al. |
| 5,316,000 A | 5/1994 | Chapelon et al. |
| 5,320,607 A | 6/1994 | Ishibashi |
| 5,323,642 A | 6/1994 | Condon |
| 5,342,380 A | 8/1994 | Hood |
| 5,352,436 A | 10/1994 | Wheatley et al. |
| 5,354,307 A | 10/1994 | Porowski |
| 5,383,858 A | 1/1995 | Reilly et al. |
| 5,385,561 A | 1/1995 | Cerny |
| 5,409,126 A | 4/1995 | DeMars |
| 5,413,574 A | 5/1995 | Fugo |
| 5,415,160 A | 5/1995 | Ortiz et al. |
| 5,417,654 A | 5/1995 | Kelman |
| 5,419,761 A | 5/1995 | Narayanan et al. |
| 5,419,777 A | 5/1995 | Hofling et al. |
| 5,380,411 A | 6/1995 | Schlief |
| 5,425,580 A | 6/1995 | Beller |
| 5,437,640 A | 8/1995 | Louis |
| 5,441,490 A | 8/1995 | Svedman |
| 5,449,351 A | 9/1995 | Zohmann |
| 5,457,041 A | 10/1995 | Ginaven et al. |
| 5,476,368 A | 12/1995 | Rabenau et al. |
| 5,478,315 A | 12/1995 | Brothers |
| 5,494,038 A | 2/1996 | Wang et al. |
| 5,507,790 A | 4/1996 | Weiss |
| 5,522,797 A | 6/1996 | Grimm |
| 5,533,981 A | 7/1996 | Mandro et al. |
| 5,545,123 A | 8/1996 | Oritz et al. |
| 5,556,406 A | 9/1996 | Gordon et al. |
| 5,562,693 A | 10/1996 | Devlin et al. |
| 5,569,242 A | 10/1996 | Lax et al. |
| 5,571,131 A | 11/1996 | Ek et al. |
| 5,573,002 A | 11/1996 | Pratt |
| 5,573,497 A | 11/1996 | Chapelon |
| 5,590,657 A | 1/1997 | Cain |
| 5,601,526 A | 2/1997 | Chapelon |
| 5,601,584 A | 2/1997 | Obaji et al. |
| 5,607,441 A | 3/1997 | Sierocuk et al. |
| 5,634,911 A | 6/1997 | Hermann et al. |
| 5,639,443 A | 6/1997 | Schutt et al. |
| 5,649,947 A | 7/1997 | Auerbach et al. |
| 5,662,646 A | 9/1997 | Fumich |
| 5,681,026 A | 10/1997 | Durand |
| 5,690,657 A | 11/1997 | Koepnick |
| 5,695,460 A | 12/1997 | Siegel et al. |
| 5,716,326 A | 2/1998 | Dannan |
| 5,733,572 A | 3/1998 | Unger et al. |
| 5,755,753 A | 5/1998 | Knowlton |
| 5,766,198 A | 6/1998 | Li |
| 5,772,688 A | 6/1998 | Muroki |
| 5,778,894 A | 7/1998 | Dorogi et al. |
| 5,792,140 A * | 8/1998 | Tu .......................... A61B 18/08 606/41 |
| 5,795,311 A | 8/1998 | Wess |

(56) References Cited

U.S. PATENT DOCUMENTS

| | | | |
|---|---|---|---|
| 5,797,627 A | 8/1998 | Salter et al. | |
| 5,810,765 A * | 9/1998 | Oda | A61M 1/0058 604/22 |
| 5,817,054 A | 10/1998 | Grimm | |
| 5,817,115 A | 10/1998 | Nigam | |
| 5,827,204 A | 10/1998 | Grandia et al. | |
| 5,827,216 A | 10/1998 | Lgo et al. | |
| 5,865,309 A | 2/1999 | Futagawa et al. | |
| 5,871,524 A | 2/1999 | Knowlton | |
| 5,884,631 A | 3/1999 | Silberg | |
| 5,885,232 A | 3/1999 | Guitay | |
| 5,902,272 A | 5/1999 | Eggers et al. | |
| 5,911,700 A | 6/1999 | Mozsary et al. | |
| 5,911,703 A | 6/1999 | Slate et al. | |
| 5,918,757 A | 7/1999 | Przytulla et al. | |
| 5,919,219 A | 7/1999 | Knowlton | |
| 5,935,142 A | 8/1999 | Hood | |
| 5,935,143 A | 8/1999 | Hood | |
| 5,942,408 A | 8/1999 | Christensen et al. | |
| 5,948,011 A | 9/1999 | Knowlton | |
| 5,961,475 A | 10/1999 | Guitay | |
| 5,964,776 A | 10/1999 | Peyman | |
| 5,976,153 A | 11/1999 | Truong | |
| 5,976,163 A | 11/1999 | Nigam | |
| 5,980,517 A | 11/1999 | Gough | |
| 5,983,131 A | 11/1999 | Weaver et al. | |
| 5,984,915 A | 11/1999 | Loeb et al. | |
| 5,993,423 A | 11/1999 | Choi | |
| 5,997,501 A | 12/1999 | Gross et al. | |
| 6,035,897 A | 3/2000 | Kozyuk | |
| 6,039,048 A | 3/2000 | Silberg | |
| 6,042,539 A | 3/2000 | Harper et al. | |
| 6,047,215 A | 4/2000 | McClure et al. | |
| 6,048,337 A | 4/2000 | Svedman | |
| 6,066,131 A | 5/2000 | Mueller et al. | |
| 6,071,239 A | 6/2000 | Cribbs et al. | |
| 6,083,236 A | 7/2000 | Feingold | |
| 6,102,887 A | 8/2000 | Altman | |
| 6,113,558 A | 9/2000 | Rosenschein et al. | |
| 6,117,152 A | 9/2000 | Huitema | |
| RE36,939 E | 10/2000 | Tachibana et al. | |
| 6,128,958 A | 10/2000 | Cain | |
| 6,132,755 A | 10/2000 | Eicher et al. | |
| 6,139,518 A | 10/2000 | Mozary et al. | |
| 6,155,989 A | 12/2000 | Collins | |
| 6,162,232 A | 12/2000 | Shadduck | |
| 6,176,854 B1 | 1/2001 | Cone | |
| 6,183,442 B1 | 2/2001 | Athanasiou et al. | |
| 6,193,672 B1 | 2/2001 | Clement | |
| 6,200,291 B1 | 3/2001 | Di Pietro | |
| 6,200,313 B1 | 3/2001 | Abe et al. | |
| 6,230,540 B1 | 3/2001 | Weber | |
| 6,210,393 B1 | 4/2001 | Brisken | |
| 6,214,018 B1 | 4/2001 | Kreizman et al. | |
| 6,237,604 B1 | 5/2001 | Burnside et al. | |
| 6,241,753 B1 | 6/2001 | Knowlton | |
| 6,254,580 B1 | 7/2001 | Svedman | |
| 6,254,614 B1 | 7/2001 | Jesseph | |
| 6,258,056 B1 | 7/2001 | Turley et al. | |
| 6,258,378 B1 | 7/2001 | Schneider et al. | |
| 6,261,272 B1 | 7/2001 | Gross et al. | |
| 6,273,877 B1 | 8/2001 | West et al. | |
| 6,277,116 B1 | 8/2001 | Utely et al. | |
| 6,280,401 B1 | 8/2001 | Mahurkar | |
| 6,287,274 B1 | 9/2001 | Sussman et al. | |
| 6,287,456 B1 | 9/2001 | Gussman et al. | |
| 6,302,863 B1 | 10/2001 | Tankovich | |
| 6,309,355 B1 | 10/2001 | Cain et al. | |
| 6,311,090 B1 | 10/2001 | Knowlton | |
| 6,312,439 B1 | 11/2001 | Gordon | |
| 6,315,756 B1 | 11/2001 | Tankovich | |
| 6,315,777 B1 * | 11/2001 | Comben | 606/41 |
| 6,319,230 B1 | 11/2001 | Palasis et al. | |
| 6,321,109 B2 | 11/2001 | Ben-Haim et al. | |
| 6,325,801 B1 | 12/2001 | Monnier | |
| 6,338,710 B1 | 1/2002 | Takahashi et al. | |
| 6,350,276 B1 | 2/2002 | Knowlton | |
| 6,366,206 B1 | 4/2002 | Ishikawa et al. | |
| 6,375,634 B1 | 4/2002 | Carroll | |
| 6,377,854 B1 | 4/2002 | Knowlton | |
| 6,377,855 B1 | 4/2002 | Knowlton | |
| 6,381,497 B1 | 4/2002 | Knowlton | |
| 6,381,498 B1 | 4/2002 | Knowlton | |
| 6,387,380 B1 | 5/2002 | Knowlton | |
| 6,391,020 B1 | 5/2002 | Kurtz et al. | |
| 6,391,023 B1 | 5/2002 | Weber et al. | |
| 6,397,098 B1 | 5/2002 | Uber, III et al. | |
| 6,405,090 B1 | 6/2002 | Knowlton | |
| 6,409,665 B1 | 6/2002 | Scott et al. | |
| 6,413,216 B1 | 7/2002 | Cain et al. | |
| 6,413,255 B1 | 7/2002 | Stern | |
| 6,425,912 B1 | 7/2002 | Knowlton | |
| 6,340,466 B1 | 8/2002 | Knowlton | |
| 6,430,446 B1 | 8/2002 | Knowlton | |
| 6,432,101 B1 | 8/2002 | Weber et al. | |
| 6,436,078 B1 | 8/2002 | Svedman | |
| 6,436,578 B2 | 8/2002 | Svedman | |
| 6,438,424 B1 | 8/2002 | Knowlton | |
| 6,440,096 B1 | 8/2002 | Lastovich et al. | |
| 6,440,121 B1 | 8/2002 | Weber et al. | |
| 6,443,914 B1 | 9/2002 | Costantino | |
| 6,450,979 B1 | 9/2002 | Miwa | |
| 6,451,240 B1 | 9/2002 | Sherman et al. | |
| 6,453,202 B1 | 9/2002 | Knowlton | |
| 6,454,730 B1 | 9/2002 | Hechel et al. | |
| 6,461,350 B1 | 10/2002 | Underwood et al. | |
| 6,461,378 B1 | 10/2002 | Knowlton | |
| 6,464,680 B1 | 10/2002 | Brisken et al. | |
| 6,470,216 B1 | 10/2002 | Knowlton | |
| 6,470,218 B1 | 10/2002 | Behl | |
| 6,479,034 B1 | 11/2002 | Unger et al. | |
| 6,500,141 B1 | 12/2002 | Irion et al. | |
| 6,506,611 B2 | 1/2003 | Bienert et al. | |
| 6,511,463 B1 | 1/2003 | Wood et al. | |
| 6,514,220 B2 | 2/2003 | Melton | |
| 6,517,498 B1 | 2/2003 | Burbank et al. | |
| 6,537,242 B1 | 3/2003 | Palmer | |
| 6,537,246 B1 | 3/2003 | Unger et al. | |
| 6,544,201 B1 | 4/2003 | Guitay | |
| 6,569,176 B2 | 5/2003 | Jesseph | |
| 6,572,839 B2 | 6/2003 | Sugita | |
| 6,575,930 B1 | 6/2003 | Trombley, III et al. | |
| 6,582,442 B2 | 6/2003 | Simon et al. | |
| 6,585,678 B1 | 7/2003 | Tachibana et al. | |
| 6,599,305 B1 | 7/2003 | Feingold | |
| 6,602,251 B2 | 8/2003 | Burbank et al. | |
| 6,605,079 B2 | 8/2003 | Shanks et al. | |
| 6,605,080 B1 | 8/2003 | Altschuler et al. | |
| 6,607,498 B2 | 8/2003 | Eschel | |
| 6,611,707 B1 | 8/2003 | Prausnitz et al. | |
| 6,615,166 B1 | 9/2003 | Guheen et al. | |
| 6,623,457 B1 | 9/2003 | Rosenberg | |
| 6,626,854 B2 | 9/2003 | Friedman et al. | |
| 6,629,949 B1 | 10/2003 | Douglas | |
| 6,638,767 B2 | 10/2003 | Unger et al. | |
| 6,645,162 B2 | 11/2003 | Friedman et al. | |
| 6,662,054 B2 | 12/2003 | Kreindel et al. | |
| 6,663,616 B1 | 12/2003 | Roth et al. | |
| 6,663,618 B2 | 12/2003 | Weber et al. | |
| 6,663,820 B2 | 12/2003 | Arias et al. | |
| 6,685,657 B2 | 2/2004 | Jones | |
| 6,695,781 B2 | 2/2004 | Rabiner | |
| 6,695,808 B2 | 2/2004 | Tom | |
| 6,702,779 B2 | 3/2004 | Connelly et al. | |
| 6,725,095 B2 | 4/2004 | Fenn et al. | |
| 6,730,061 B1 | 5/2004 | Cuschieri et al. | |
| 6,743,211 B1 | 6/2004 | Prausnitz et al. | |
| 6,743,214 B2 | 6/2004 | Bernabei | |
| 6,743,215 B2 | 6/2004 | Bernabei | |
| 6,749,624 B2 | 6/2004 | Knowlton | |
| 6,770,071 B2 | 8/2004 | Woloszko et al. | |
| 6,780,171 B2 | 8/2004 | Gabel et al. | |
| 6,687,537 B2 | 9/2004 | Bernabei | |
| 6,795,727 B2 | 9/2004 | Giammarusti | |

(56) References Cited

U.S. PATENT DOCUMENTS

| | | |
|---|---|---|
| 6,795,728 B2 | 9/2004 | Chornenky et al. |
| 6,817,988 B2 | 11/2004 | Bergeron et al. |
| 6,826,429 B2 | 11/2004 | Johnson et al. |
| 6,855,133 B2 | 2/2005 | Svedman |
| 6,882,884 B1 | 4/2005 | Mosk et al. |
| 6,889,090 B2 | 5/2005 | Kreindal |
| 6,892,099 B2 | 5/2005 | Jaafar et al. |
| 6,896,659 B2 | 5/2005 | Conston et al. |
| 6,896,666 B2 | 5/2005 | Kochamba |
| 6,896,674 B1 | 5/2005 | Woloszko et al. |
| 6,883,729 B2 | 6/2005 | Putvinski et al. |
| 6,902,554 B2 | 6/2005 | Huttner |
| 6,905,480 B2 | 6/2005 | McGuckin et al. |
| 6,910,671 B1 | 6/2005 | Korkus et al. |
| 6,916,328 B2 * | 7/2005 | Brett .............................. 606/167 |
| 6,918,907 B2 | 7/2005 | Kelly et al. |
| 6,918,908 B2 | 7/2005 | Bonner et al. |
| 6,920,883 B2 | 7/2005 | Bessette et al. |
| 6,926,683 B1 | 8/2005 | Kochman et al. |
| 6,931,277 B1 | 8/2005 | Yuzhakov et al. |
| 6,945,937 B2 | 9/2005 | Culp et al. |
| 6,957,186 B1 | 10/2005 | Guheen et al. |
| 6,960,205 B2 | 11/2005 | Jahns et al. |
| 6,971,994 B1 | 12/2005 | Young |
| 6,974,450 B2 | 12/2005 | Weber |
| 6,994,691 B2 | 2/2006 | Ejlerson |
| 6,994,705 B2 | 2/2006 | Nebis et al. |
| 7,066,922 B2 | 6/2006 | Angel et al. |
| 7,083,580 B2 | 8/2006 | Bernabei |
| 7,115,108 B2 | 10/2006 | Wilkinson et al. |
| 7,149,698 B2 | 12/2006 | Guheen et al. |
| 7,153,306 B2 | 12/2006 | Ralph et al. |
| 7,169,115 B2 | 1/2007 | Nobis et al. |
| 7,184,614 B2 | 2/2007 | Slatkine |
| 7,184,826 B2 | 2/2007 | Cormier et al. |
| 7,186,252 B2 | 3/2007 | Nobis et al. |
| 7,217,265 B2 | 5/2007 | Hennings et al. |
| 7,223,275 B2 | 5/2007 | Shiuey |
| 7,226,446 B1 | 6/2007 | Mody et al. |
| 7,237,855 B2 | 7/2007 | Vardon |
| 7,238,183 B2 | 7/2007 | Kreindel |
| 7,250,047 B2 | 7/2007 | Anderson et al. |
| 7,252,641 B2 | 8/2007 | Thompson et al. |
| 7,258,674 B2 | 8/2007 | Cribbs et al. |
| 7,278,991 B2 | 10/2007 | Morris et al. |
| 7,306,095 B1 | 12/2007 | Bourque et al. |
| 7,315,826 B1 | 1/2008 | Guheen et al. |
| 7,331,951 B2 | 2/2008 | Eschel et al. |
| 7,335,158 B2 | 2/2008 | Taylor |
| 7,338,551 B2 | 3/2008 | Kozyuk |
| 7,347,855 B2 | 3/2008 | Eschel et al. |
| 7,351,295 B2 | 4/2008 | Pawlik et al. |
| 7,374,551 B2 | 5/2008 | Liang |
| 7,376,460 B2 | 5/2008 | Bernabei |
| 7,392,080 B2 | 6/2008 | Eppstein et al. |
| 7,410,476 B2 | 8/2008 | Wilkinson et al. |
| 7,419,798 B2 | 9/2008 | Ericson |
| 7,437,189 B2 | 10/2008 | Matsumura et al. |
| 7,442,192 B2 | 10/2008 | Knowlton |
| 7,452,358 B2 | 11/2008 | Stern et al. |
| 7,455,663 B2 | 11/2008 | Bikovsky |
| 7,470,237 B2 | 12/2008 | Beckman et al. |
| 7,473,251 B2 | 1/2009 | Knowlton et al. |
| 7,479,104 B2 | 1/2009 | Lau et al. |
| 7,625,354 B2 | 1/2009 | Hochman |
| 7,494,488 B2 | 2/2009 | Weber |
| 7,507,209 B2 | 3/2009 | Nezhat et al. |
| 7,524,318 B2 | 4/2009 | Young et al. |
| 7,546,918 B2 | 6/2009 | Gollier et al. |
| 7,559,905 B2 | 7/2009 | Kagosaki et al. |
| 7,566,318 B2 | 7/2009 | Haefner |
| 7,585,281 B2 | 9/2009 | Nezhat et al. |
| 7,588,547 B2 | 9/2009 | Deem et al. |
| 7,588,557 B2 | 9/2009 | Nakao |
| 7,601,128 B2 | 10/2009 | Deem et al. |
| 7,625,371 B2 | 12/2009 | Morris et al. |
| 7,678,097 B1 | 3/2010 | Peluso et al. |
| 7,740,600 B2 | 6/2010 | Slatkine et al. |
| 7,762,964 B2 | 7/2010 | Slatkine et al. |
| 7,762,965 B2 | 7/2010 | Slatkine et al. |
| 7,770,611 B2 | 8/2010 | Houwaert et al. |
| 7,771,374 B2 | 8/2010 | Slatkine et al. |
| 7,824,348 B2 | 11/2010 | Barthe et al. |
| 7,828,827 B2 | 11/2010 | Gartstein et al. |
| 7,842,008 B2 | 11/2010 | Clarke et al. |
| 7,901,421 B2 | 3/2011 | Shiuey et al. |
| 7,935,139 B2 | 5/2011 | Slatkine et al. |
| 7,938,824 B2 | 5/2011 | Chornenky et al. |
| 7,967,763 B2 | 6/2011 | Deem et al. |
| 7,985,199 B2 | 7/2011 | Kornerup et al. |
| 7,988,667 B2 | 8/2011 | Imai |
| 8,025,658 B2 | 9/2011 | Chong et al. |
| 8,083,715 B2 | 12/2011 | Sonoda et al. |
| 8,086,322 B2 | 12/2011 | Schouenborg |
| 8,103,355 B2 | 1/2012 | Mulholland et al. |
| 8,127,771 B2 | 3/2012 | Hennings |
| 8,133,191 B2 | 3/2012 | Rosenberg et al. |
| 8,256,429 B2 | 9/2012 | Hennings et al. |
| 8,348,867 B2 | 1/2013 | Deem et al. |
| 8,357,146 B2 | 1/2013 | Hennings et al. |
| 8,366,643 B2 | 2/2013 | Deem et al. |
| 8,401,668 B2 | 3/2013 | Deem et al. |
| 8,406,894 B2 | 3/2013 | Johnson et al. |
| 8,439,940 B2 | 5/2013 | Chomas et al. |
| 8,518,069 B2 | 8/2013 | Clark, III et al. |
| 8,535,302 B2 | 9/2013 | Ben-Haim et al. |
| 8,540,705 B2 | 9/2013 | Mehta |
| 8,573,227 B2 | 11/2013 | Hennings et al. |
| 8,608,737 B2 | 12/2013 | Mehta et al. |
| 8,636,665 B2 | 1/2014 | Slayton et al. |
| 8,652,123 B2 | 2/2014 | Gurtner et al. |
| 8,663,112 B2 | 3/2014 | Slayton et al. |
| 8,671,622 B2 | 3/2014 | Thomas |
| 8,672,848 B2 | 3/2014 | Slayton et al. |
| 8,676,338 B2 | 3/2014 | Levinson |
| 8,685,012 B2 | 4/2014 | Hennings et al. |
| 8,753,339 B2 | 6/2014 | Clark, III et al. |
| 8,758,366 B2 | 6/2014 | McLean et al. |
| 8,771,263 B2 | 7/2014 | Epshtein et al. |
| 8,825,176 B2 | 9/2014 | Johnson et al. |
| 8,834,547 B2 | 9/2014 | Anderson et al. |
| 8,868,204 B2 | 10/2014 | Edoute et al. |
| 8,882,753 B2 | 11/2014 | Mehta et al. |
| 8,882,758 B2 | 11/2014 | Nebrigie et al. |
| 8,894,678 B2 | 11/2014 | Clark, III et al. |
| 8,900,261 B2 | 12/2014 | Clark, III et al. |
| 8,900,262 B2 | 12/2014 | Clark, III et al. |
| 8,979,882 B2 | 3/2015 | Drews et al. |
| 9,011,473 B2 | 4/2015 | Clark, III et al. |
| 9,039,722 B2 | 5/2015 | Clark, III et al. |
| 9,345,456 B2 | 5/2016 | Tsonton et al. |
| 9,364,246 B2 | 6/2016 | Clark, III et al. |
| 2001/0001829 A1 | 5/2001 | Sugimura et al. |
| 2001/0004702 A1 | 6/2001 | Peyman |
| 2001/0014805 A1 | 8/2001 | Burbank et al. |
| 2001/0053887 A1 | 12/2001 | Douglas et al. |
| 2002/0029053 A1 | 3/2002 | Gordon |
| 2002/0082528 A1 | 6/2002 | Frieman et al. |
| 2002/0082589 A1 | 6/2002 | Friedman et al. |
| 2002/0099356 A1 | 7/2002 | Unger et al. |
| 2002/0111569 A1 | 8/2002 | Rosenschein |
| 2002/0120238 A1 | 8/2002 | McGuckin et al. |
| 2002/0120260 A1 | 8/2002 | Morris et al. |
| 2002/0120261 A1 | 8/2002 | Morris et al. |
| 2002/0130126 A1 | 9/2002 | Rosenberg |
| 2002/0134733 A1 | 9/2002 | Kerfoot |
| 2002/0137991 A1 | 9/2002 | Scarantino |
| 2002/0143326 A1 | 10/2002 | Foley et al. |
| 2002/0169394 A1 | 11/2002 | Eppstein et al. |
| 2002/0177846 A1 | 11/2002 | Muller |
| 2002/0185557 A1 | 12/2002 | Sparks |
| 2002/0193784 A1 | 12/2002 | McHale et al. |
| 2002/0193831 A1 | 12/2002 | Smith, III |
| 2003/0006677 A1 | 1/2003 | Okuda et al. |

(56) References Cited

U.S. PATENT DOCUMENTS

| | | |
|---|---|---|
| 2003/0009153 A1 | 1/2003 | Briskin et al. |
| 2003/0069502 A1 | 4/2003 | Makin et al. |
| 2003/0074023 A1 | 4/2003 | Kaplan et al. |
| 2003/0083536 A1 | 5/2003 | Eschel et al. |
| 2003/0120269 A1 | 7/2003 | Bessette et al. |
| 2003/0130628 A1 | 7/2003 | Duffy |
| 2003/0130655 A1 | 7/2003 | Woloszko et al. |
| 2003/0130711 A1* | 7/2003 | Pearson et al. ............... 607/101 |
| 2003/0139740 A1 | 7/2003 | Kreindel |
| 2003/0139755 A1 | 7/2003 | Dybbs |
| 2003/0153905 A1 | 8/2003 | Edwards et al. |
| 2003/0153960 A1 | 8/2003 | Chornenky et al. |
| 2003/0158566 A1 | 8/2003 | Brett |
| 2003/0171670 A1 | 9/2003 | Gumb et al. |
| 2003/0187371 A1 | 10/2003 | Vortman et al. |
| 2003/0212350 A1 | 11/2003 | Tadlock |
| 2003/0228254 A1 | 12/2003 | Klaveness et al. |
| 2003/0233083 A1 | 12/2003 | Houwaert |
| 2003/0233110 A1 | 12/2003 | Jesseph |
| 2004/0006566 A1 | 1/2004 | Taylor et al. |
| 2004/0019299 A1 | 1/2004 | Ritchart et al. |
| 2004/0019371 A1 | 1/2004 | Jaafar et al. |
| 2004/0023844 A1 | 2/2004 | Pettis et al. |
| 2004/0030263 A1 | 2/2004 | Dubrul et al. |
| 2004/0039312 A1 | 2/2004 | Hillstead et al. |
| 2004/0158150 A1 | 2/2004 | Rabiner |
| 2004/0058882 A1 | 3/2004 | Eriksson et al. |
| 2004/0073144 A1 | 4/2004 | Carava |
| 2004/0073206 A1 | 4/2004 | Foley et al. |
| 2004/0079371 A1 | 4/2004 | Gray |
| 2004/0097967 A1 | 5/2004 | Ignon |
| 2004/0106867 A1 | 6/2004 | Eschel et al. |
| 2004/0120861 A1 | 6/2004 | Petroff |
| 2004/0122483 A1 | 6/2004 | Nathan et al. |
| 2004/0138712 A1 | 7/2004 | Tamarkin et al. |
| 2004/0162546 A1 | 8/2004 | Liang et al. |
| 2004/0162554 A1 | 8/2004 | Lee et al. |
| 2004/0167558 A1 | 8/2004 | Igo et al. |
| 2004/0186425 A1 | 9/2004 | Schneider et al. |
| 2004/0200909 A1 | 10/2004 | McMillan et al. |
| 2004/0202576 A1 | 10/2004 | Aceti et al. |
| 2004/0206365 A1 | 10/2004 | Knowlton |
| 2004/0210214 A1 | 10/2004 | Knowlton |
| 2004/0215101 A1 | 10/2004 | Rioux et al. |
| 2004/0215110 A1 | 10/2004 | Kreindel |
| 2004/0220512 A1 | 11/2004 | Kreindel |
| 2004/0236248 A1 | 11/2004 | Svedman |
| 2004/0236252 A1 | 11/2004 | Muzzi et al. |
| 2004/0026293 A1 | 12/2004 | Laugharn et al. |
| 2004/0243159 A1 | 12/2004 | Shiuey |
| 2004/0243160 A1 | 12/2004 | Shiuey et al. |
| 2004/0251566 A1 | 12/2004 | Kozyuk |
| 2004/0253148 A1 | 12/2004 | Leaton |
| 2004/0253183 A1 | 12/2004 | Uber, III et al. |
| 2004/0264293 A1 | 12/2004 | Laugharn et al. |
| 2005/0010197 A1 | 1/2005 | Lau et al. |
| 2005/0015024 A1 | 1/2005 | Babaev |
| 2005/0027242 A1 | 2/2005 | Gabel et al. |
| 2005/0033338 A1 | 2/2005 | Ferree |
| 2005/0049543 A1 | 3/2005 | Anderson et al. |
| 2005/0055018 A1 | 3/2005 | Kreindal |
| 2005/0080333 A1 | 4/2005 | Piron et al. |
| 2005/0085748 A1 | 4/2005 | Culp et al. |
| 2005/0102009 A1 | 5/2005 | Costantino |
| 2005/0131439 A1 | 6/2005 | Brett et al. |
| 2005/0136548 A1 | 6/2005 | McDevitt |
| 2005/0137525 A1 | 6/2005 | Wang et al. |
| 2005/0139142 A1 | 6/2005 | Kelley et al. |
| 2005/0154309 A1 | 7/2005 | Etchells et al. |
| 2005/0154314 A1 | 7/2005 | Quistgaard |
| 2005/0154443 A1 | 7/2005 | Quistgaard et al. |
| 2005/0163711 A1 | 7/2005 | Nycz et al. |
| 2005/0182385 A1 | 8/2005 | Epley |
| 2005/0182462 A1 | 8/2005 | Chornenky et al. |
| 2005/0191252 A1 | 9/2005 | Mutsui |
| 2005/0197633 A1* | 9/2005 | Schwartz ............... A61M 5/158 604/264 |
| 2005/0197663 A1 | 9/2005 | Schwartz et al. |
| 2005/0203497 A1 | 9/2005 | Speeg |
| 2005/0215987 A1 | 9/2005 | Slatkine |
| 2005/0234527 A1 | 10/2005 | Svedman |
| 2005/0256536 A1 | 11/2005 | Grundeman et al. |
| 2005/0268703 A1 | 12/2005 | Funck et al. |
| 2006/0100555 A1 | 1/2006 | Cagle et al. |
| 2006/0036300 A1 | 2/2006 | Kreindel |
| 2006/0058678 A1 | 3/2006 | Vitek et al. |
| 2006/0074313 A1 | 4/2006 | Slayton |
| 2006/0074314 A1 | 4/2006 | Slayton et al. |
| 2006/0079921 A1 | 4/2006 | Nezhat et al. |
| 2006/0094988 A1 | 5/2006 | Tosaya et al. |
| 2006/0102174 A1 | 5/2006 | Hochman |
| 2006/0111744 A1 | 5/2006 | Makin et al. |
| 2006/0122509 A1 | 6/2006 | Desilets |
| 2006/0206040 A1 | 9/2006 | Greenberg |
| 2006/0206117 A1 | 9/2006 | Harp |
| 2006/0211958 A1 | 9/2006 | Rosenberg et al. |
| 2006/0235371 A1 | 10/2006 | Wakamatsu et al. |
| 2006/0235732 A1 | 10/2006 | Miller et al. |
| 2006/0241672 A1 | 10/2006 | Zadini et al. |
| 2006/0241673 A1 | 10/2006 | Zadini |
| 2006/0259102 A1 | 11/2006 | Slatkine |
| 2006/0264809 A1 | 11/2006 | Hausmann et al. |
| 2006/0264926 A1 | 11/2006 | Kochamba |
| 2006/0293722 A1 | 12/2006 | Slatkine et al. |
| 2007/0005091 A1 | 1/2007 | Zadini et al. |
| 2007/0010810 A1 | 1/2007 | Kochamba |
| 2007/0016234 A1 | 1/2007 | Daxer |
| 2007/0027411 A1 | 2/2007 | Ella et al. |
| 2007/0031482 A1 | 2/2007 | Castro et al. |
| 2007/0035201 A1 | 2/2007 | Desilets et al. |
| 2007/0041961 A1 | 2/2007 | Hwang et al. |
| 2007/0043295 A1 | 2/2007 | Chomas et al. |
| 2007/0055156 A1 | 3/2007 | Desilets et al. |
| 2007/0055179 A1 | 3/2007 | Deem et al. |
| 2007/0060989 A1 | 3/2007 | Deem et al. |
| 2007/0118077 A1 | 5/2007 | Clarke et al. |
| 2007/0118166 A1 | 5/2007 | Nobis et al. |
| 2007/0129708 A1 | 6/2007 | Edwards et al. |
| 2007/0142881 A1 | 6/2007 | Hennings |
| 2007/0156096 A1 | 7/2007 | Sonoda et al. |
| 2007/0179515 A1 | 8/2007 | Matsutani et al. |
| 2007/0191827 A1 | 8/2007 | Lischinsky |
| 2007/0197907 A1 | 8/2007 | Bruder et al. |
| 2007/0197917 A1 | 8/2007 | Bagge |
| 2007/0239075 A1 | 10/2007 | Rosenberg et al. |
| 2007/0239079 A1 | 10/2007 | Manstein et al. |
| 2007/0255355 A1 | 11/2007 | Altshuler et al. |
| 2007/0270745 A1 | 11/2007 | Nezhat et al. |
| 2007/0282318 A1 | 12/2007 | Spooner et al. |
| 2007/0293849 A1 | 12/2007 | Hennings et al. |
| 2008/0014627 A1 | 1/2008 | Merchant et al. |
| 2008/0015435 A1 | 1/2008 | Cribbs et al. |
| 2008/0015624 A1 | 1/2008 | Sonoda et al. |
| 2008/0027328 A1 | 1/2008 | Klopotek et al. |
| 2008/0027384 A1 | 1/2008 | Wang et al. |
| 2008/0058603 A1 | 3/2008 | Edelstein et al. |
| 2008/0058851 A1 | 3/2008 | Edelstein et al. |
| 2008/0091126 A1 | 4/2008 | Greenburg |
| 2008/0091182 A1 | 4/2008 | Mehta |
| 2008/0109023 A1 | 5/2008 | Greer |
| 2008/0147084 A1 | 6/2008 | Bleich et al. |
| 2008/0172012 A1* | 7/2008 | Hiniduma-Lokuge ..................... B21G 1/08 604/272 |
| 2008/0183164 A1 | 7/2008 | Elkins et al. |
| 2008/0188835 A1 | 8/2008 | Hennings et al. |
| 2008/0195036 A1 | 8/2008 | Merchant et al. |
| 2008/0200845 A1 | 8/2008 | Sokka et al. |
| 2008/0200864 A1 | 8/2008 | Holzbaur et al. |
| 2008/0215039 A1 | 9/2008 | Slatkine et al. |
| 2008/0234609 A1 | 9/2008 | Kreindel et al. |
| 2008/0249526 A1 | 10/2008 | Knowlton |
| 2008/0262527 A1 | 10/2008 | Eder et al. |
| 2008/0269668 A1 | 10/2008 | Keenan et al. |

(56) References Cited

U.S. PATENT DOCUMENTS

| | | |
|---|---|---|
| 2008/0269687 A1 | 10/2008 | Chong et al. |
| 2008/0306476 A1 | 12/2008 | Hennings et al. |
| 2008/0319356 A1 | 12/2008 | Cain et al. |
| 2008/0319358 A1 | 12/2008 | Lai |
| 2009/0012434 A1 | 1/2009 | Anderson |
| 2009/0018522 A1 | 1/2009 | Weintraub et al. |
| 2009/0024192 A1 | 1/2009 | Mulholland |
| 2009/0048544 A1 | 2/2009 | Rybyanets et al. |
| 2009/0088823 A1 | 4/2009 | Barak et al. |
| 2009/0093864 A1 | 4/2009 | Anderson |
| 2009/0118722 A1 | 5/2009 | Ebbers et al. |
| 2009/0124973 A1 | 5/2009 | D'Agostino et al. |
| 2009/0125013 A1 | 5/2009 | Sypniewski et al. |
| 2009/0156958 A1 | 6/2009 | Mehta |
| 2009/0171255 A1 | 7/2009 | Rybyanets et al. |
| 2009/0192441 A1 | 7/2009 | Gelbart |
| 2009/0198189 A1 | 8/2009 | Simons et al. |
| 2009/0221938 A1 | 9/2009 | Rosenberg et al. |
| 2009/0240188 A1 | 9/2009 | Hyde et al. |
| 2009/0248004 A1 | 10/2009 | Altshuler et al. |
| 2009/0270789 A1 | 10/2009 | Maxymiv et al. |
| 2009/0275879 A1 | 11/2009 | Deem et al. |
| 2009/0275899 A1 | 11/2009 | Deem et al. |
| 2009/0275967 A1 | 11/2009 | Stokes et al. |
| 2009/0326439 A1 | 12/2009 | Chomas et al. |
| 2009/0326441 A1 | 12/2009 | Iliescu et al. |
| 2009/0326461 A1 | 12/2009 | Gresham |
| 2010/0004536 A1 | 1/2010 | Rosenberg |
| 2010/0016761 A1 | 1/2010 | Rosenberg |
| 2010/0017750 A1 | 1/2010 | Rosenberg et al. |
| 2010/0022999 A1 | 1/2010 | Gollnick et al. |
| 2010/0030262 A1 | 2/2010 | McLean et al. |
| 2010/0049178 A1 | 2/2010 | Deem et al. |
| 2010/0057056 A1 | 3/2010 | Gurtner et al. |
| 2010/0081881 A1 | 4/2010 | Murray |
| 2010/0137799 A1 | 6/2010 | Imai |
| 2010/0210915 A1 | 8/2010 | Caldwell et al. |
| 2010/0228182 A1 | 9/2010 | Clark, III et al. |
| 2010/0228207 A1 | 9/2010 | Ballakur et al. |
| 2010/0331875 A1 | 12/2010 | Sonoda et al. |
| 2011/0028898 A1 | 2/2011 | Clark et al. |
| 2011/0295230 A1 | 12/2011 | O'Dea |
| 2012/0022504 A1 | 1/2012 | Epshtein et al. |
| 2012/0116375 A1 | 5/2012 | Hennings |
| 2012/0136280 A1 | 5/2012 | Rosenberg et al. |
| 2012/0136282 A1 | 5/2012 | Rosenberg et al. |
| 2012/0165725 A1 | 6/2012 | Chomas et al. |
| 2012/0197242 A1 | 8/2012 | Rosenberg |
| 2012/0277587 A1 | 11/2012 | Adanny et al. |
| 2012/0316547 A1 | 12/2012 | Hennings et al. |
| 2013/0023855 A1 | 1/2013 | Hennings et al. |
| 2013/0096596 A1 | 4/2013 | Schafer |
| 2013/0197315 A1 | 8/2013 | Foley |
| 2013/0197427 A1 | 8/2013 | Merchant et al. |
| 2013/0296744 A1 | 11/2013 | Taskinen et al. |
| 2014/0025050 A1 | 1/2014 | Anderson |
| 2014/0031803 A1 | 1/2014 | Epshtein et al. |
| 2014/0107742 A1 | 4/2014 | Mehta |
| 2014/0228834 A1 | 8/2014 | Adanny et al. |
| 2014/0249609 A1 | 9/2014 | Zarsky et al. |
| 2014/0257272 A1 | 9/2014 | Clark, III et al. |
| 2014/0276693 A1 | 9/2014 | Altshuler et al. |
| 2014/0277025 A1 | 9/2014 | Clark, III et al. |
| 2014/0277047 A1 | 9/2014 | Clark, III et al. |
| 2014/0277048 A1 | 9/2014 | Clark, III et al. |
| 2014/0316393 A1 | 10/2014 | Levinson |
| 2015/0064165 A1 | 3/2015 | Perry et al. |

FOREIGN PATENT DOCUMENTS

| | | |
|---|---|---|
| CN | 1159908 | 9/1997 |
| CN | 1484520 A | 3/2004 |
| CN | 1823687 | 8/2006 |
| CN | 2007/20159899 | 12/2007 |
| CN | 2011/31982 | 10/2008 |
| CN | 101795641 | 8/2010 |
| DE | 3838530 A1 | 5/1990 |
| DE | 4426421 | 2/1996 |
| EP | 148116 A1 | 7/1985 |
| EP | 0224934 A1 | 12/1986 |
| EP | 0278074 A2 | 11/1987 |
| EP | 0327490 A1 | 2/1989 |
| EP | 0384831 A3 | 2/1990 |
| EP | 0953432 | 3/1999 |
| GB | 1216813 | 12/1970 |
| GB | 1577551 | 2/1976 |
| GB | 2327614 | 3/1999 |
| JP | 57-139358 | 8/1982 |
| JP | 2180275 | 7/1990 |
| JP | 5215591 | 8/1993 |
| JP | 2000-190976 | 7/2000 |
| JP | 2001516625 | 10/2001 |
| JP | 2002-017742 | 1/2002 |
| JP | 2002-528220 | 9/2002 |
| JP | 2004283420 | 10/2004 |
| JP | 2005087519 | 4/2005 |
| WO | 8002365 A1 | 11/1980 |
| WO | 8905159 A1 | 6/1989 |
| WO | 8905160 A1 | 6/1989 |
| WO | 8909593 A1 | 10/1989 |
| WO | 9001971 A1 | 3/1990 |
| WO | 9209238 A1 | 6/1992 |
| WO | 9515118 A1 | 6/1995 |
| WO | WO 9729701 | 8/1997 |
| WO | WO9913936 | 3/1999 |
| WO | WO9942138 | 8/1999 |
| WO | WO 00/25692 | 5/2000 |
| WO | WO 2000/36982 | 6/2000 |
| WO | WO 03/030984 | 4/2003 |
| WO | WO 03/941597 | 5/2003 |
| WO | 2003047689 A1 | 6/2003 |
| WO | 2004000116 A1 | 12/2003 |
| WO | 2004069153 A2 | 8/2004 |
| WO | WO2005/009865 | 2/2005 |
| WO | 2005105818 A1 | 11/2005 |
| WO | WO2005/105282 | 11/2005 |
| WO | WO3047689 | 11/2005 |
| WO | WO2006/053588 | 5/2006 |
| WO | WO2007/035177 | 3/2007 |
| WO | 2007102161 A2 | 9/2007 |
| WO | WO2008/055243 | 5/2008 |
| WO | WO2008/139303 | 11/2008 |
| WO | WO2010/020021 | 2/2010 |
| WO | WO2011/017663 | 2/2011 |
| WO | WO2012/087506 | 6/2012 |
| WO | WO2013/059263 | 4/2013 |
| WO | WO 2014/009875 | 1/2014 |
| WO | WO 2014/009826 | 3/2014 |
| WO | WO 2014/060977 | 4/2014 |
| WO | WO 2014/097288 | 6/2014 |
| WO | WO 2014/108888 | 7/2014 |
| WO | WO 2014/141229 | 9/2014 |

OTHER PUBLICATIONS

Bindal, Dr. V. V., et al., Environmental Health Criteria for Ultrasound, International Programme on Chemical Safety, 1982, pp. 1-153, World Health Organization.

Cartensen, E.L., Allerton Conference for Ultrasonics in Biophysics and Bioengineering: Cavitation, Ultrasound in Med. & Biol., 1987, pp. 687-688, vol. 13, Pergamon Journals, Ltd.

Chang, Peter P., et al., Thresholds for Inertial Cavitation in Albunex Suspensions Under Pulsed Ultrasound Conditions, IEEE Transactions on Ultrasonics, Ferroelectrics, and Frequency Control, Jan. 2001, pp. 161-170, vol. 48, No. 1.

Chen, Wen-Shiang, Ultrasound Contrast Agent Behavior near the Fragmentation Threshold, 2000 IEEE Ultrasonics Symposium, 2000, pp. 1935-1938.

Dijkmans, P.A., et al., Microbubbles and Ultrasound: From Diagnosis to Therapy, Eur J Echocardiography, 2004, pp. 245-256, vol. 5, Elsevier Ltd., The Netherlands.

(56) References Cited

OTHER PUBLICATIONS

Feril, L.B., et al., Enhanced Ultrasound-Induced Apoptosis and Cell Lysis by a Hypnotic Medium, International Journal of Radiation Biology, Feb. 2004, pp. 165-175, vol. 2, Taylor & Francis Ltd., United Kingdom.

Feril, Jr., Loreto B., et al., Biological Effects of Low Intensity Ultrasound: The Mechanism Involved, and its Implications on Therapy and on Biosafety of Ultrasound, J. Radiat. Res., 2004, pp. 479-489, vol. 45.

Forsberg, Ph.D., F., et al., On the Usefulness of the Mechanical Index Displayed on Clinical Ultrasound Scanners for Predicting Contrast Microbubble Destruction, J Ultrasound Med, 2005, pp. 443-450, vol. 24, American Institute of Ultrasound in Medicine.

Hanscom, D.R., Infringement Search Report prepared for K. Angela Macfarlane, Esq., Chief Technology Counsel, The Foundry, Nov. 15, 2005.

Hexsel, M.D., Doris Maria, et al., Subcision: a Treatment for Cellulite, International journal of Dermatology 2000, pp. 539-544, vol. 39.

Holland, Christy K., et al., In Vitro Detection of Cavitation Induced by a Diagnostic Ultrasound System, IEEE Transactions on Ultrasonics, Ferroelectrics, and Frequency Control, Jan. 1992, pp. 95-101, vol. 39, No. 1.

Lawrence, M.D., N., et al., The Efficacy of External Ultrasound-Assisted Liposuction: A Randomized Controlled Trial, Dermatol Surg, Apr. 2000, pp. 329-332, vol. 26, Blackwell Science, Inc.

Michaelson, Solomon M., et al., Fundamental and Applied Aspects of Nonionizing Radiation, Rochester International Conference on Environmental Toxicity, 75h, 1974, pp. 275-299, Plenum Press, New York and London.

Miller, Douglas L., A Review of the Ultrasonic Bioeffects of Microsonation, Gas-Body Activiation, andRelated Cavitation-Like Phenomena, Ultrasound in Med. & Biol., 1987, pp. 443-470, vol. 13, Pergamon Journals Ltd.

Miller, Douglas L., et al., Further Investigations of ATP Release From Human Erythrocytes Exposed to Ultrasonically Activated Gas-Filled Pores, Ultrasound in Med. & Biol., 1983, pp. 297-307, vol. 9, No. 3, Pergamon Press Ltd., Great Britain.

Miller, Douglas L., Gas Body Activation, Ultrasonics, Nov. 1984, pp. 261-269, vol. 22, No. 6, Butterworth & Co. Ltd.

Miller, Douglas L., Microstreaming Shear as a Mechanism of Cell Death in Elodea Leaves Exposed to Ultrasound, Ultrasound in Med. & Biol., 1985, pp. 285-292, vol. 11, No. 2, Pergamon Press, U.S.A.

Miller, Douglas L., et al., On the Oscillation Mode of Gas-filled Micropores, J. Acoust. Soc. Am., 1985, pp. 946-953, vol. 77 (3).

Miller, Morton W., et al., A Review of In Vitro Bioeffects of Inertial Ultrasonic Cavitation From a Mechanistic Perspective, Ultrasound in Med. & Biol., 1996, pp. 1131-1154, vol. 22, No. 9.

Nyborg, Dr. Wesley L., Physical Mechanisms for Biological Effects of Ultrasound, HEW Publicaton (FDA) 78-8062, Sep. 1977, pp. 1-59, U.S. Department of Health, Education, and Welfare, Rockville, Maryland.

Rohrich, M.D., R.J., et al., Comparative Lipoplasty Analysis of in Vivo-Treated Adipose Tissue, Plastic and Reconstructive Surgery, May 2000, pp. 2152-2158, vol. 105, No. 6.

Scheinfeld, M.D., J.D. Faad, N.S., Liposuction Techniques: External Ultrasound-Assisted, eMedicine.com, Inc., 2005.

Villarraga, M.D., H.R., et al., Destruction of Contrast Microbubbles During Ultrasound Imaging at Conventional Power Output, Journal of the American Society of Echocardiography, Oct. 1997, pp. 783-791.

Vivino, Alfred A., et al., Stable Cavitation at low Ultrasonic Intensities Induces Cell Death and Inhibits 3H-TdR Incorporation by Con-A-Stimulated Murine Lymphocytes In Vitro, Ultrasound in Med. & Biol., 1985, pp. 751-759, vol. 11, No. 5, Pergamon Press Ltd.

Internet Web Site—www.icin.nl/read/project_21, The Interuniversity Cardiology Institute of the Netherlands, 3 pgs., visited Dec. 22, 2005.

Internet Web Site—www.turnwoodinternational.com/Cellulite.htm, Acthyderm Treating Cellulite, Aug. 5, 2005, 4 pgs., visited Jan. 12, 2006.

Letters to the Editor re on the Thermal Motions of Small Bubbles, Ultrasound in Med. & Biol., 1984, pp. L377-L379, Pergamon Press Ltd., U.S.A.

Patent Search, CTX System Microbubble Cavitation, Nov. 11, 2005.

Report, Carstensen, E.L., Biological Effects of Acoustic Cavitation, University of Rochester, Rochester, New York, May 13-16, 1985.

Boyer, J. et al., Undermining in Cutaneous Surgery, Dermatol Surg 27:1, Jan. 2001, pp. 75-78, Blackwell Science, Inc.

http://www.thefreedictionary.com/chamber, definition of the term "chamber" retrieved Jun. 16, 2013.

International Search Report dated Apr. 9, 2012 frorn corresponding International Patent Application No. PCT/US11/62449.

Khan, M. et al., Treatment of cellulite—Part I. Pathophysiology, J Am Acad Dermatol, 2009, vol. 62, No. 3, pp. 361-370.

Khan, M. et al., Treatment of cellulite—Part II. Advances and controversies, J Am Acad Dermatol, 2009, vol. 62, No. 3, pp. 373-384.

Orentreich, D. et al., Subcutaneous Incisionless (Subcision) Surgery for the Correction of Depressed Scars and Wrinkles, Dermatol Surg, 1995:21,1995, pp. 543-549, Esevier Science Inc.

Brown, Ph.D., S., Director of Plastic Surgery Research, UT Southwestern Medical Center, Dallas, USA, What Happens After Treatment With the UltroShape Device, UltraShape Ltd., Tel Aviv, Israel (2005).

Sasaki, Gordon H. MD, Comparison of Results of Wire Subcision Peformed Alone, With Fills, and/or With Adjacent Surgical Procedures, Aesthetic Surgery Journal, vol. 28, No. 6, Nov./Dec. 2008, p. 619-626.

Hexsel, D. et al, Side-By-Side Comparison of Areas with and without Cellulite Depressions Using Magnetic Resonance Imaging, American Society for Dermatologic Surgery, Inc., 2009, pp. 1-7,Wiley Periodicals, Inc.

Green, Jeremy B. et al. Therapeutic approaches to cellulite. Seminars in Cutaneous Medicine and Surgery, vol. 34, Sep. 2015.

Green, Jeremy B. et al. Cellfina observations: pearls and pitfalls, Seminars in Cutaneouse Medicine and Surgery, vol. 34, Sep. 2015.

Kaminer, Michael S. et al. Multicenter Pivotal Study of Vacuum-Assisted Precise Tissue Release for the Treatment of Cellulite. American Society for Dermatologic Surgery, Inc. Sermatol Surg 2015:41:336-347 (2015).

Weaver, James C. Electroporation; a general phenomenon for manipulating cells and tissues. J Cell Biochem. Apr. 1993; 51(4):426-35.

\* cited by examiner

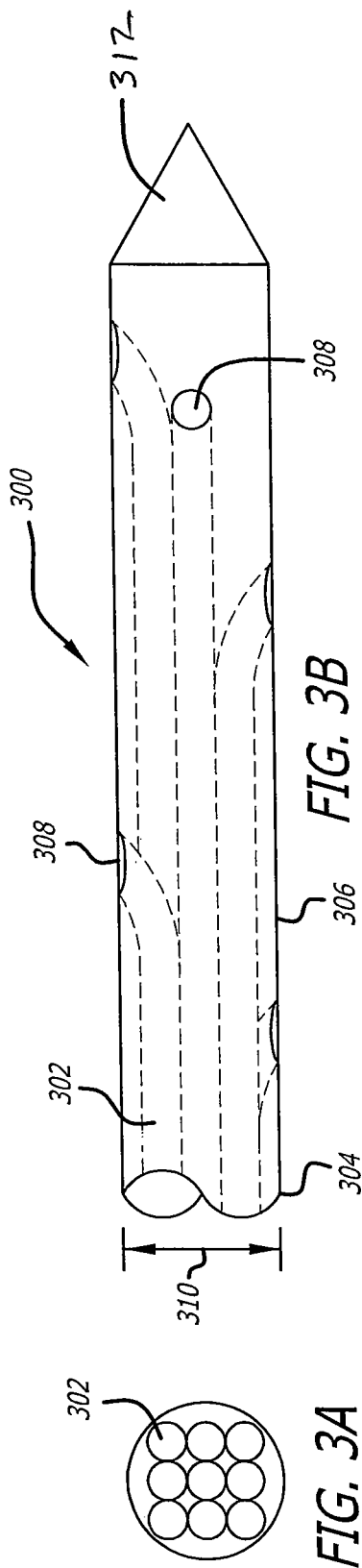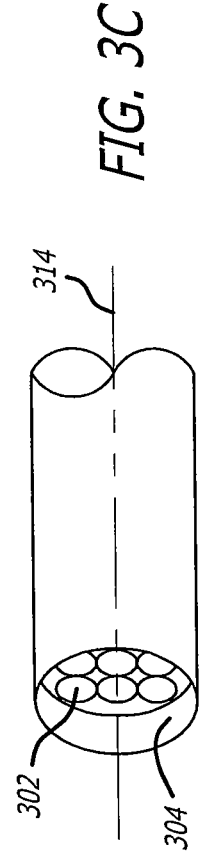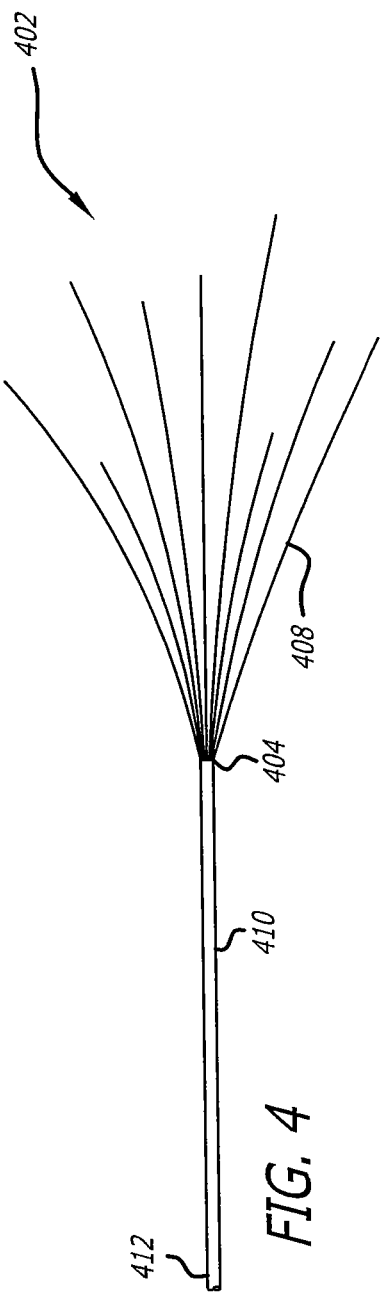

HIGH PRESSURE PRE-BURST FOR IMPROVED FLUID DELIVERY

CROSS-REFERENCES TO RELATED APPLICATIONS

This application is a continuation-in-part and claims priority from U.S. application Ser. No. 11/515,634, filed Sep. 5, 2006, now abandoned, and from U.S. application Ser. No. 11/334,794, filed Jan. 17, 2006, now U.S. Pat. No. 7,588,547, both of which are incorporated by reference in their entirety.

BACKGROUND

It has been discovered that the prominence of fibrous septae within the immediate subdermal layers restricts fluid permeability between respective chambers of fat cells. Although these fibrous structures do not necessarily isolate neighboring chambers, localized pockets are nevertheless created by the structures and fluid flow is substantially restricted to the chamber proximate the injection site. It has been further discovered that these structures are not generally impermeable to a fluid. Accordingly, it has been discovered that a substantial amount of pressure utilizing the device and method herein described will penetrate neighboring chambers and beyond and the fat cells therein to provide enhancement of therapeutic treatments.

SUMMARY OF THE INVENTION

According to a first embodiment, a device is disclosed, including a needle having at least two holes along a side of the needle, wherein the holes increase in diameter toward a distal end of the needle. The holes at the distal end of the needle are, in some aspects, larger in area $A_i$ than those near a proximal end, such that $A_3 > A_2 > A_1$ where $\Sigma A_i \geq A_{needle}$, wherein $A_{needle}$ is the cross-sectional area of the needle. In one aspect, a sum of areas of the holes is greater than the area of a needle surface proximal to the holes. The holes may be staggered or linearly disposed along a side of the needle, and the device may be made of a rigid or flexible material.

In one aspect, a plurality of elongated elements are disposed within the needle and capable of movement from a first retracted configuration within the needle to a second extended configuration outside the needle from each respective hole, wherein the distal ends of the elongated elements are farther apart from each other in the extended configuration than in the retracted configuration. At least one of the plurality of elongated elements may be an electrode, and each electrode may be at least partially electrically insulated from the other elongated elements. In some embodiments the plurality of elongated elements is one of a cutting element or a harmonic scalpel.

The needle may comprise a series of interior capillaries originating at a point proximal an end of a needle shaft, wherein each interior capillary traverses a length of the shaft to terminate at a respective output port. Each of the plurality of elongated elements disposed within the needle may be at least partially disposed within a respective capillary, and each elongated element is capable of movement from a first retracted configuration within the needle to a second extended configuration outside the needle from each respective hole, wherein the distal ends of the elongated elements are farther apart from each other in the extended configuration than in the retracted configuration. At least one of the plurality of elongated elements can be an electrode, wherein each capillary is electrically insulated from the series of interior capillaries.

Also disclosed is a method of infusing a solution into a treatment area including percutaneously inserting into the treatment area a needle having at least two holes along a side of the needle, injecting a treatment solution through the needle into the treatment area with sufficient pressure to infuse the solution between at least one fibrous structure and at least one chamber of adipose tissue. The needle may be at least partially withdrawn prior to injecting the treatment solution.

At least two tines may be extended through the shaft of the needle and through the at least two holes so that each of the tines disrupts at least one tissue outside the needle in the treatment area. The method further comprises at least partially retracting the at least two tines back into the shaft of the needle.

In some aspects, the shaft comprises multiple capillaries traversing a length of the shaft, each capillary terminating at a respective output port, wherein the holes along the side of the needle is represented by respective output ports. The method further comprises extending the at least two tines through the multiple capillaries and respective output ports, so that each of the tines disrupts at least one tissue outside the needle in the treatment area, and then at least partially retracting the each of the at least two tines back into the multiple capillaries.

Injecting the treatment solution may be timed to a pressure function rectangular in shape with little rise and fall times, whereby the pressure may be delivered at a maximum level for all times during the injection. The method may further comprise Injecting a second treatment solution through the needle into the treatment area, and applying an energy source to the treatment area from a source external to the treatment area, wherein the energy source is selected from the group consisting of ultrasound, RF, heat, electricity, or light.

A group of interleaved functions may be provided including a high-pressure burst, a solution infusion, and a treatment. The group may be performed one or more times. The high pressure burst is represented by injecting the treatment solution and the treatment includes injecting a third solution or applying an energy to the treatment area, and the high pressure burst is timed to a pressure function, the solution infusion is timed to an infusion function, and the treatment is timed to a treatment function, wherein each function is rectangular in shape with little rise and fall times. Alternatively, the high-level burst may be performed first, followed by a group of interleaved functions including the solution infusion and the treatment.

BRIEF DESCRIPTION OF THE DRAWINGS

FIGS. 3A-3C depict the needle with internal capillaries and output ports.

FIG. 4 depicts the tines of the present invention.

DETAILED DESCRIPTION OF THE PREFERRED EMBODIMENTS

Figure 1A:
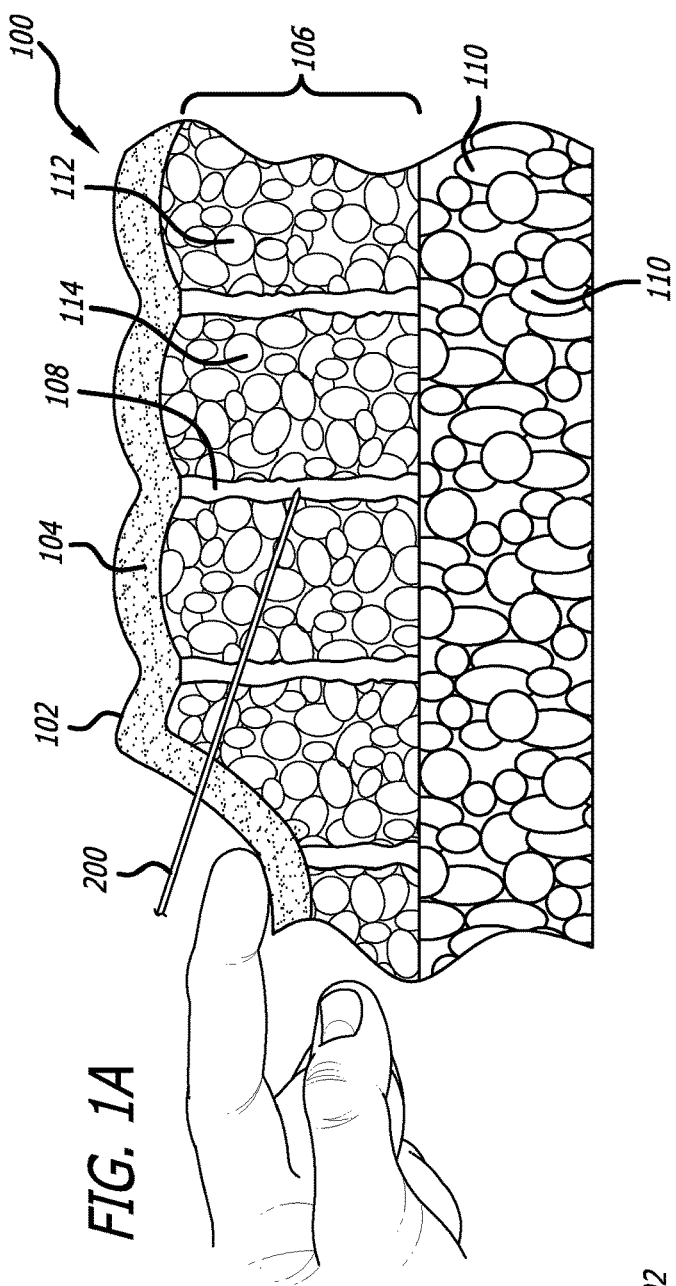
FIGS. 1A and 1B depict the device of the present invention in use in a treatment area.
Figure 1B:
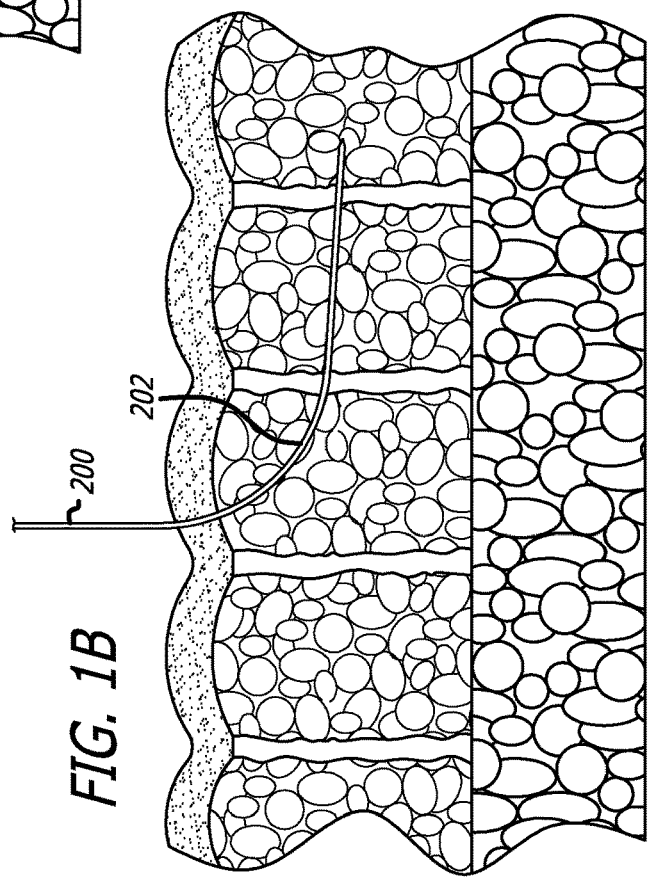

Referring first to FIGS. 1A and 1B, a cross section of a portion of a normal subcutaneous tissue region 100 is shown, including the epidermis 102, dermis 104, subcutaneous fat 106, fibrous septae 108, and deeper fat layers 110. The subcutaneous tissue also includes vascularity, microcirculation, and lymph drainage. The dermis interfaces with the fatty subcutaneous connective tissue that attaches to the dermal layers via substantially vertical septae 108 (collagenous fibers). The subcutaneous fatty tissue 106 is compartmentalized into chambers 112 of adipose tissue (fat) separated by the fibers of the septae. These chambers can increase in size due to the presence of increased adipocytes (fat cells) 114 or swell due to retained fluid. The increase in chamber size may cause tension on the septae and ultimately dimpling at the epidermal surface as the fatty regions swell and the septae thicken under the tension. Microcirculation and lymphatic drainage may then become impaired, further exacerbating the local metabolic pathology. As shown in FIG. 1A, the subcutaneous fat layer is swollen and septae tightened, leading to the irregular skin surface characteristic of cellulite. A reserve or deeper fat layer 110 is disposed beneath the subcutaneous fat 106 and may also contribute to a skin irregularity. The deeper fat layer is also included herein as one of the subcutaneous tissues that may be treated by at least one embodiment of the present invention.

In one aspect of the invention, treatment of subcutaneous tissue includes disruption of the fibrous septae 108 to lessen the tension on the skin surface 102 that contributes to dimpling. In another aspect, treatment of subcutaneous tissue includes disruption of the subcutaneous fat cells 114. In yet another aspect, treatment of subcutaneous tissue includes disruption of a deeper fat layer 110 for overall surface contouring.

The needle of the present invention utilizes an elongated needle-type device 200 capable of being inserted into a subdermal treatment area. In some aspects, the tissue to be treated may be injected anywhere between the dermis layer and the deep fat layer. In one aspect the needle may be precisely placed in the subdermal fat, i.e. the shallow fat layer which is between 1 and 20 mm below the dermis or in the deep fat layer which is between X and Y mm below the dermis. According to one aspect, the treatment area 106 is typically located in a subdermal fat layer between 1 mm and 5 mm below a dermis. The needle may be inserted through, or proximal to, one or more fibrous structures 108 responsible for creating a chamber of fat cells 112 in the treatment area, or through or proximal to a group of fat cells 114 in the treatment area. In another aspect, the needle is placed between 5 mm and 20 mm below the dermis. In other aspects, the tissue to be treated may be injected anywhere between the superficial fat layer and the muscle layer. In yet other aspects, the tissue to be treated may be injected anywhere between the dermal layer and the muscle layer.

The device 200 has an thin elongated shaft which is configured to be percutaneously inserted through dermis 104 and into the subdermal treatment area. As depicted by FIG. 1A device 200 is preferably inserted in a manner such that it remains parallel to the overall surface of the skin. This may be accomplished by using one hand to depress the skin while inserting the device from a side of the depression such that it can then be percutaneously inserted laterally through the dermis. A second hand (or one or more fingers) may cover the epidermis to stabilize device 200 as it moves within the treatment area parallel to the surface and second hand.

In an embodiment depicted by FIG. 1B, the insertion device has a flexible portion 202 which allows the device 200 to bend on entry into the treatment area such that it is more easily maneuvered within the treatment area parallel to the surface of epidermis 102. Device 200 is percutaneously inserted into the treatment area and bent slightly so that the distal end having the fluid ports remains parallel to the skin, between the skin and the lower muscle layers below the subcutaneous fat layer. In such embodiment, device 200 may include a flexible portion, or device 200 may be a flexible cannula.

Device 200 includes a needle 210, or needle 300, which may be attached to a syringe or other fluid delivery system. Needle 210, 300 may be only a portion (preferably the end) of device 200 or may be the equivalent of device 200. Because needle 210, 300 may make up, in some embodiments, the entirety of device 200, needle 210, 300 may also be used sometimes herein synonymously with device 200. Needle 210, 300 is used to inject solution directly into the treatment area described above. Referring to FIGS. 2A through 2E, needle 210 has a single hole or port (not shown) at its distal end, however, needle 210 more preferably has more than one hole or port 204, located along at least one side of needle 210. Multiple ports 204 are used to allow a broader distribution of fluid delivered by device 200 throughout the area of treatment during an injection. The solution will infuse into the subcutaneous tissues, including the subcutaneous fat and adipose tissue. The solution may be infused directly into the fat cells making them larger and more vulnerable to injury and/or infused over a wider distribution of area to be treated.

Figure 2A:
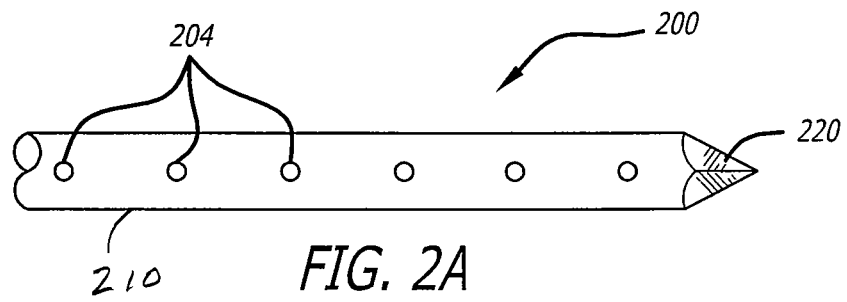
FIGS. 2A-2E depict embodiments of the needle of the present invention.
Figure 2B:
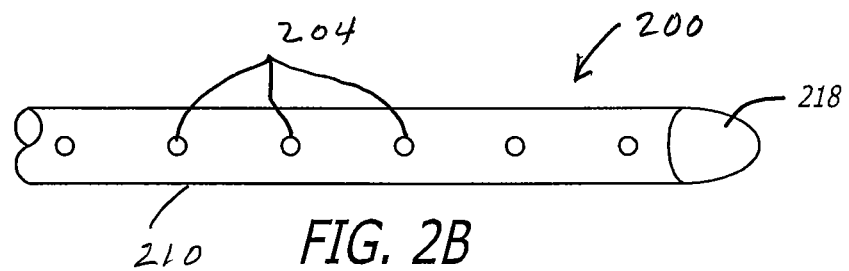
Figure 2C:
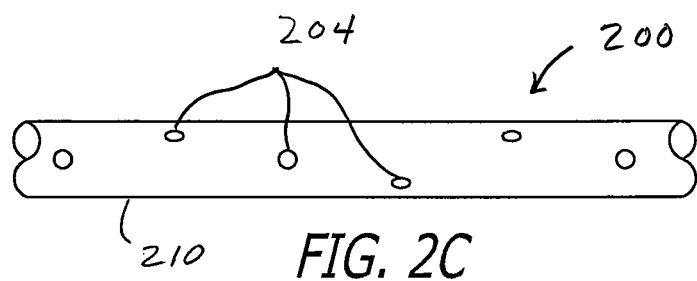
Figure 2D:
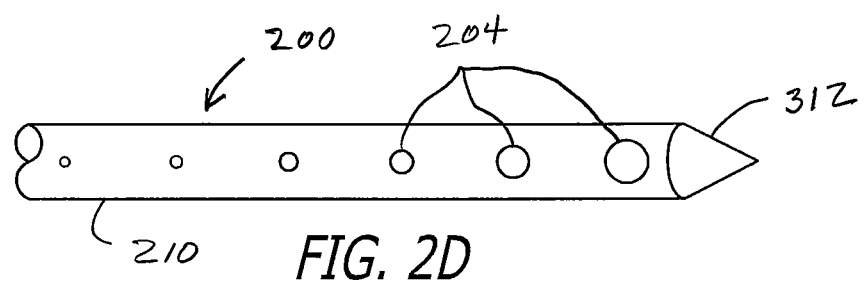
Figure 2E:
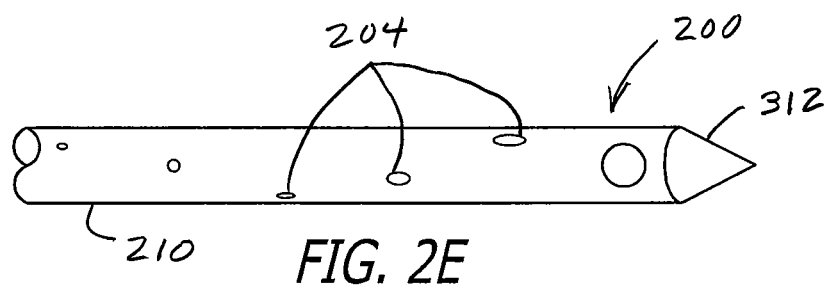

In some embodiments, such as depicted in FIGS. 2A, 2B and 2D, the ports 204 may be aligned on a side of device 200 and/or needle 210 so that when device 200 is positioned in the subcutaneous treatment area it can be further oriented such that the infusion occurs predominately in the plane of the fat, parallel to the surface of the skin, ensuring that the fluid is further distributed over the largest possible area. In other embodiments, as depicted in FIGS. 2C and 2E, the ports 204 may be staggered. One particular advantage of a staggered configuration is an increased mechanical strength. Another advantage is the ability to infuse solution throughout the treatment area without necessitating perfect alignment of needle 210. Other scenarios are foreseen where chambers 112 may exist in an at least partially stacked configuration in which infusion in a non-parallel manner may be appropriate to reach the chambers and be effective for treatment.

Similar to hypodermic needles, the needle 210 is preferably made from a stainless-steel tube drawn through progressively smaller dies to make the needle. The ports can be drilled after the forming process is completed or, in some cases, created during the forming process by typical progressive die technique, including, for instance, a piercing operation. The needle may also be embedded in a plastic or aluminum or stainless steel hub at its most proximal end to allow attachment to a syringe barrel or other fluid delivery device by means of a press-fit or twist-on fitting. In embodiments incorporating a flexible portion 202 or cannula, device 200 (including the needle) or those flexible portions thereof are preferably made from a flexible material such as plastic or polymeric material, or a polyurethane or polyurethane hybrid co-polymer, sterile silicone, or any material known in the cannula art.

As depicted by FIG. 2A, the end of needle 210 may be pointed or beveled to create a sharp tip to allow the needle easily penetrate the skin. FIG. 2B depicts an embodiment of needle 210 including a blunt tip 218. In some instances, a blunt tipped needle 210 may be inserted into a pre-existing opening in the dermis and blunt tip 218 used to break the fibrous structures by blunt dissection. It is understood that by using blunt dissection the surrounding blood vessels are less likely to be severed but will only be stretched and thus the surrounding structures will be less traumatized by not being sharply cut. It is expected that this will result in less trauma to the patient as well as lesser complications during the procedure. In other embodiments, blunt tip 218 is used merely to avoid any cutting of tissue during the injection of the fluid.

In some embodiments the needle or cannula may include a trocar tip 220 for introduction of the device to the treatment area. This is particularly advantageous in those embodiments where a smaller gauge (e.g., 7 gauge) needle is used, or in embodiments in which the delivery device is a tubular member or a catheter or trocar. The trocar tip can be fashioned at the distal end of the device or it may be passed inside a cannula to function as a portal for the subsequent placement of other devices herein described.

Turning to FIGS. 3A though 3C, in some aspects device 200 is a needle 300 (incorporated within or in addition to needle 210) further formed to include of a series of interior capillaries 302 originating at a point near or at the proximal end 304 of the needle shaft with each interior capillary 302 traversing the length of the shaft 306 to terminate at a respective output port 308. In this embodiment the diameter 310 of needle 300 may be fixed to a slightly larger nominal outer diameter, e.g., 9 to 12 gauge, to accommodate multiple internal capillaries 302 each including a much smaller nominal outer diameter, e.g., 26 to 34 gauge. Larger or smaller sizes of needle 300 and/or interior capillaries 302 may be used depending on the desired properties of the fluid used in the device as well as the tolerance of the ultimate patient and/or skin-type. For example, in one embodiment in which the needle has an outer diameter of 9 gauge (3.7 mm) the needle may have up to 12 interior capillaries each including an outer diameter of 31 gauge (0.26 mm). As depicted in FIG. 3C, the internal capillaries 302 are preferably configured to be grouped in an array about a common axis 314 of the body of device 200. For ease of manufacture and predictability of delivery, the middle-most capillaries extend to the most distal ends 134 of the needle/device 200, 300, with the outer most capillaries 302 terminating at a more proximal location 304. Referring back to FIG. 3B, in embodiments in which a staggered port configuration is used, the capillaries 302 terminate at respective ports 308 along a side of needle 300, and respective to the capillary location, and in respect to a common axis 314. In a parallel port configuration the capillaries are further preferably modified to bend to accordingly terminate at a respective parallel port 308, with the capillaries closest to axis 314 terminating at the most distal ports and the outer-most capillaries terminating at ports at more proximal locations. Additionally, in some embodiments, the interior capillaries may be aligned at their respective ports such that the fluid leaves the port at a specified angle; e.g., 45 degrees.

In the embodiment depicted by FIGS. 3A through 3C, the needle is preferably formed in two stages. In one stage, the capillary array is formed according to the desired embodiment (e.g. parallel port or staggered port). In a second stage, the needle is formed using the process previously described. In a third stage, the capillary array may be inserted into the needle housing and sealed accordingly about its ports using micro/nano assembly techniques and/or sealed at the cavity between the interior capillaries and inner diameter of the needle housing the capillaries. In an embodiment in which the insertion device includes a flexible cannula, the capillaries will preferably include smaller flexible tubing or cannula-like structures. In this embodiment the forming process is similar, however, a parallel port configuration will typically require less construction effort due to the flexibility of the interior capillaries.

In practice, if the cavity between the proximal end of the interior capillaries and inner diameter 304 of the needle housing is filled then fluid from the fluid input location at the most proximal end of the needle can be moved with substantially equal force into each capillary and consequently out each respective port 308. It has been shown that, where microbubbles are part of the modality of the treatment solution, this configuration is particularly advantageous as forcing a fluid through a larger diameter channel (e.g., needle body interior) into a smaller capillary (e.g., each capillary 302) will increase cavitation downstream at the capillary output port thereby increasing microbubble formation in vivo as the fluid exits from the needle ports.

In yet a further aspect of the invention, device 200 may be adapted to deploy an array of tines to a subcutaneous region to be treated. Turning to FIG. 4, the array of tines 402 are selected from the group consisting of needles, electrodes, and cutting elements. Suitable tines 402 for practicing the invention are disclosed in U.S. Publication No. 2007/0060989 to Deem et al., filed Sep. 5, 2006, incorporated herein by reference. In one embodiment, each tine is an electrode providing a fanned array of electrodes.

The tine elements 408 may be deployed through the skin 102, 104 through the main shaft 306, each tine within a respective capillary 302, and "fan out" from each port 308 in an orientation substantially horizontal (parallel) to the skin surface 102 in a parallel port configuration (e.g., FIG. 2A), or fan out around the needle in a staggered port configuration (e.g., FIG. 2C). In embodiments where the tines are also electrodes, the material of device 200 and/or needle 210, 300 is electrically non-conductive or coated with a insulating coating. This prevents short circuits and heat related effects from occurring in the treatment area when the electrodes are charged an in contact with the needle housing, either internally or after deployment of the electrodes. Upon deployment of the tines and application of energy, the subcutaneous structures such as subcutaneous fat 106 or the fibrous septae 108 may be disrupted. By having each capillary electrically insulated each tine may also be positively or negatively charged so as to create a multipolar, bipolar, or monopolar electrode configuration. In a further embodiment, the needle tip geometry may be configured to shape the energy field for particular tissue disruption effects.

Using multiple tines, it is possible to treat a greater area in a shorter amount of time. The tines of the electrode device may further be adapted to be hollow to allow injection of treatment enhancing agents. The hollow tines may have further outlet ports (not shown) at the distal end of each tine as well as along the length thereof.

Referring to FIGS. 3A through 3C, device 200 including needle 300 may have a first (proximal) end 304, a second (distal) end 310 adapted for insertion into subcutaneous tissue, and one or more channels 302 longitudinally disposed therebetween. A plurality of extendable elongated elements 402 may be bundled at a proximal location 404 and second distal ends 408 that may be inserted/disposed within needle 300 and/or at a respective channel 302, and capable of movement from a first retracted configuration within needle 300 to a second extended configuration outside device 300, outward from each respective port 308, wherein the distal ends of the elongated elements 402 are farther apart from each other in the extended configuration than in the retracted configuration. The elements 408 may be inserted into capillaries 302 at a proximal end 304 of needle 300. The needle of the device may or may not include capillaries 302, whereby, in embodiments without such capillaries the elongated elements are disposed in needle housing such that the ends of the elements partially extend out from ports 204 or disposed in a tubular member 300 (e.g., FIG. 5A) having a central channel, wherein the needles are configured for movement between an extended position in which the needles protrude out from the central channel in a fanned configuration and a retracted position in which the needles are fully retracted in the central channel.

In one embodiment each tine/electrode 408 may be electrically insulated from the other by an insulative coating formed along the length and circumference of each insulated tine 408. The coating can be any insulation known in the art for electrically insulation of wire. The coating preferably will extend beyond bundling location 406 so that a relatively small portion of each respective electrode 408 extending outside needle 300 and port 308 remains exposed for maximum RF density. The array of tines may also be a tubing in which the bundled electrodes and/or tines are disposed, a shaft 410 wherein the bundled wires are retained, shaft 410 having a distal portion 404 whereby the electrodes are bundled, and a proximal portion 412. In one embodiment a connector (not shown) is provided near or at proximal location 412 for connecting each electrode to a energy delivery device such as an RF amplifier (not shown). In a further embodiment, harmonic scalpel elements 408 may be used in the array.

In yet another embodiment, one or more RF knives may be used in the array. The RF knife applies a high-frequency electric current to biological tissue as a means to cut, coagulate, desiccate, or fulgurate tissue (electrosurgery). In yet another embodiment, mechanical scalpels or cutting elements may be used in the array. The Harmonic scalpel is a cutting instrument used during surgical procedures to simultaneously cut and coagulate tissue. The instrument is capable of cutting through thicker tissue, creates less smoke, and offers good precision. The Harmonic scalpel coagulates as it cuts, and, causes less lateral thermal damage than other tools, such as a RF knife. The Harmonic scalpel cuts via vibration; i.e., the scalpel surface itself cuts through tissue by vibrating in the range of about 20,000 Hz. This vibration cuts through the tissue and seals it using protein denaturization, rather than heat.

In yet another embodiment, the tines are merely sharp cutting elements 408 that do not deliver energy, but can be extended to pierce, disrupt and/or destroy fibrous structures 108 and/or chambers 112 and/or cell groups 114 when needle 300 is positioned within the treatment area. In such an embodiment the elements 408 may or may not be insulated, and may be bound together at a junction 404 such that the cutting elements 408 can be easily inserted into capillaries 302 and/or needle 300 at proximal end 304. Shaft 410 may be used to manipulate the elements 408 within device 200. In practice, elements 408 may also be positioned parallel to the skin surface 102 and rotated about the longitudinal axis 314 (FIG. 3C) of needle 300 or retracted in a substantially parallel orientation to the skin, so that needle 300 can efficiently disrupt multiple septae 108 in one rotation or retraction. In still another embodiment device 200 can be adapted for infusion of treatment enhancing agents into the treatment area through channels 302 and ports 308. In such embodiments the tines may be extended to create canals in tissue through which a solution from device 200 can travel.

Still referring to FIG. 4, in yet a further embodiment, a tine 408, for example, a cutting element may be deployed at an acute angle to the center axis 314 of needle 300. The array of tines 402 can be collapsed for insertion through needle 300, and then expanded once placed in the subcutaneous space 106, 108, 110.

Figure 5A:
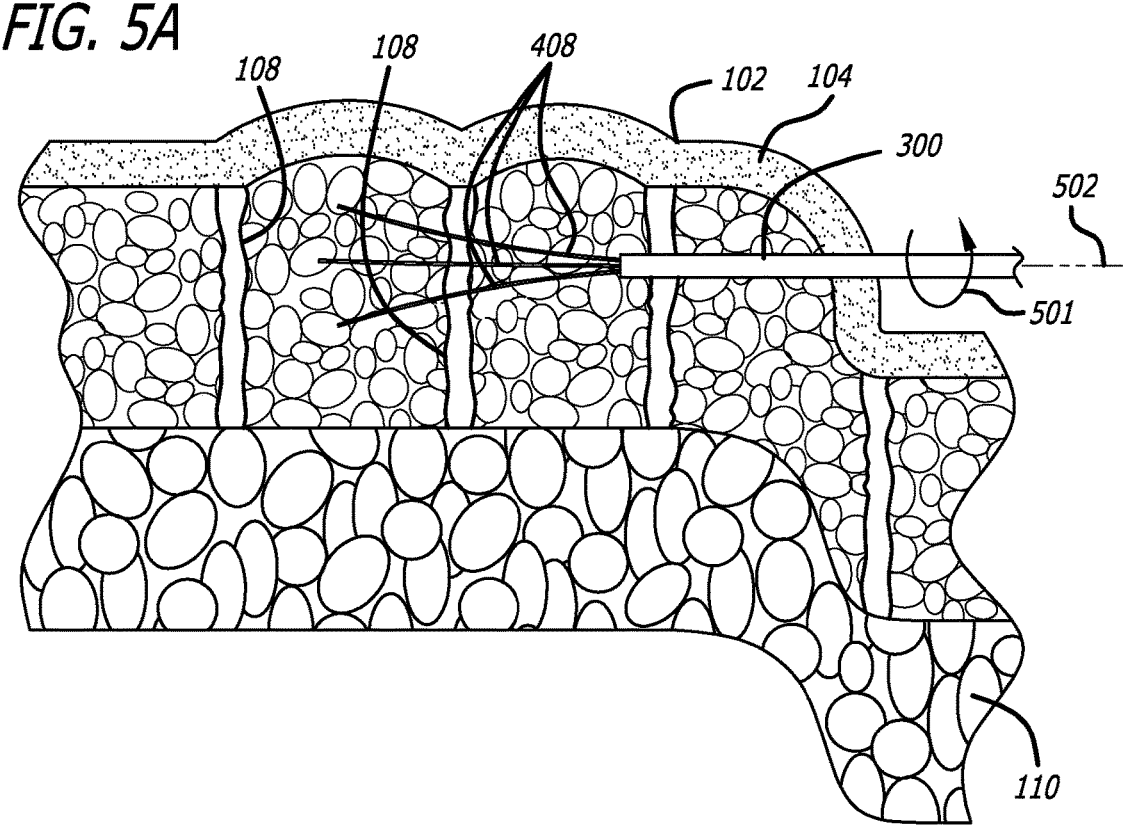
FIGS. 5A and 5B depict the tines in use in the treatment area.
Figure 5B:
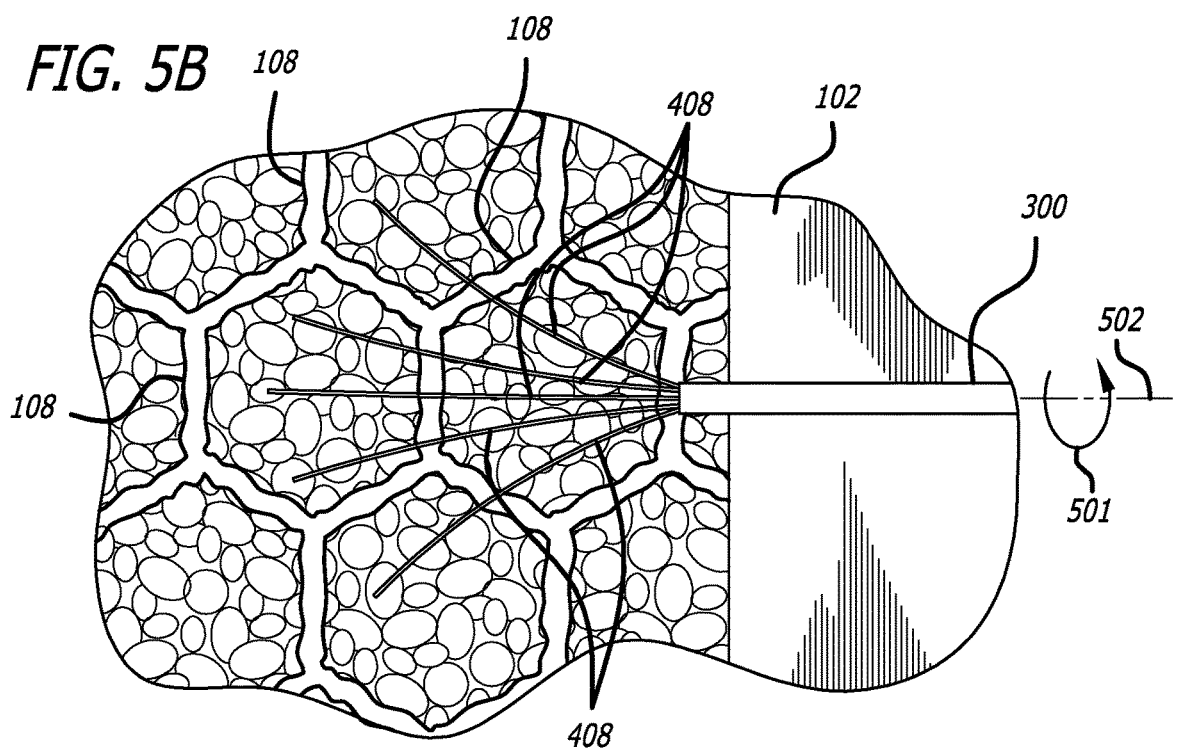

As depicted in FIGS. 5A and 5B, elements 408 may be employed through the skin 102, 104 through main tubular member or needle 210, 300, and "fan out" in an orientation substantially horizontal (parallel) to the skin surface. In at least one embodiment, upon deployment of the microneedles such that they are substantially parallel to the skin surface, the subcutaneous structures such as the fibrous septae 108 may be disrupted. Using multiple needles, it is possible to treat a greater area in a shorter amount of time. The microneedles may be configured with additional outlet ports (not shown) along the length of the microneedles. In one aspect, the needles include sharp cutting elements.

When the needles are positioned parallel to the skin surface and inserted into the subdermal treatment area the fanned element array 402 can efficiently disrupt multiple septae 108 in one deployment of elements 408 from needle 300 (e.g., FIGS. 3B and 4). In another aspect, when the needle 300 including elements 408 is rotated 501 about the axis 314 or retracted upwardly towards the epidermis 102, the fanned element array 408 can efficiently disrupt multiple septae 108 in one rotation or retraction. In at least one embodiment, some of the needles may be solid without central channels and one other may have a channel for injection. In one embodiment, at least one needle in the needle array is further configured for delivery of electrical energy through the needle to heat tissue or disrupt tissue. In one embodiment, at least a portion of the needle is electrically insulated, wherein the electrical energy is dispersed to the tissue over only a portion of the needle. The invention may also be combined with subcision procedures and device such as that disclosed in U.S. Pat. No. 6,916,328 to Brett, filed Jul. 22, 2002, and entitled "PERCUTANEOUS CELLULITE REMOVAL SYSTEM," the entirety of which is incorporated herein by reference. Combination with subcision may be particularly advantageous in areas of severe cellulite pathology. Upon expansion to its cutting configuration, as shown in FIGS. 5A and 5B, the shaft 306 is then oriented parallel to the skin surface 102 and needle 300 is pulled back, catching and cutting the septae 108 in its path. Elements 408 may be, for example, a blunt dissector, a mechanical cutter, or an energy-assisted device. In energy-assisted embodiments, any of the applicable energy modalities may be employed, including radiofrequency energy or resistive heat energy.

In one embodiment, the fan-type electrode configuration of FIGS. 5A and 5B may be deployed in conjunction with a tissue disruption device (not shown), for example, a compatible electrode or ultrasound. Suitable disruption devices for practicing the invention are disclosed in U.S. Publication Nos. 20070055180 to Deem et al., filed Jan. 17, 2006, 2007/0060989 to Deem et al., filed Sep. 5, 2006, and 2008/0200863 to Chomas et al., filed Jun. 29, 2007, all incorporated herein by reference. The tissue disruption device may be disposed outside the dermis 102, 104. In one embodiment, the fan-type electrodes 402 may be oriented such that the electric field they produce is advantageously positioned to target connective tissue such as the fibrous septae 108. In at least one embodiment the disruption device (not shown) is positively charged and the needle electrodes 408 are negatively charged. One embodiment may include needle 300 as the tissue disruption device and fan-type electrodes 402 may be deployed through the center of needle 300, electrically insulated from the polarized charge of needle 300. In this embodiment channels 302 may be excluded and electrodes 402 may extend out distal end 310. The fan-type electrodes 402 may then be rotated to mechanically assist the energy disruption of the tissue to be treated. In one embodiment the needle electrodes 402, 408 may also be electrically insulated proximally with exposed electrically active distal tips.

The current invention employs the use of a high-pressure burst of fluid in connection with the injection delivery device (capillary or non-capillary) to improve the extent of fluid distribution and to reduce pooling of fluid in the treatment area along the needle. The high-pressure burst may either be a pre-burst before a standard injection is performed, or may be high pressure burst as a means for delivering the desired fluid. The object of the device and method of the present invention is to inject fluid with a high pressure to create low resistance pathways in the tissue. Preliminary studies in gel phantom show improved separation of gel structure and improved delivery of a dye into the gel. It has also been shown that there is a broader distribution of fluid perpendicular to the needle.

A high-pressure burst may be employed prior to the injection of treatment solution so that the subsequent treatment solution is more easily infused into the treatment area. The burst solution may be a solution, such as a saline, which allows for the transport of other treatment solutions. Such treatment solutions used with the present invention may include, but are not limited to, anesthetics such as lidocaine, a surfactant, vasoconstrictive agents such as epinephrine, hypotonic saline, potassium, agitated saline, microbubbles, commercially available ultrasound contrast agents, microspheres, adipocytes, fat, autologous tissues (e.g., lysed fat cells to produce clean adipocytes to form a tissue graft to minimize hostile response from the body), PLLA, hydroxyappetite. The high-pressure burst may also be used to infuse adipocyte or other cells with, for example, a hypotonic saline, to increase their cellular diameter. Larger cells are more vulnerable to injury. Infusion may make the cell membranes more susceptible to damage by producing adipocyte swelling that results in an increase in the stress on the cell membrane. Thus, further treatments may be used to disrupt the targeted cells in the treatment area. In one embodiment, a microbubble solution may be infused into the treatment area and an energy source used to cavitate the microbubbles, causing the surrounding vulnerable cells to destruction. A preferred method of cavitation of microbubbles is disclosed in U.S. Publication No. 20070055180 to Deem et al., filed Jan. 17, 2006, incorporated herein by reference. In another embodiment an external energy source may be used to disrupt the targeted cells from a source outside the body or treatment area. Such energy sources may include, but are not limited to, RF energy, ultrasound, vibrational energy, heat, or laser. In one embodiment an electrode may be inserted into the treatment area to deliver the energy directly to, or proximal to, the cells to be treated.

Referring back to FIGS. 2A through 2E, the hole diameters of holes 204 will preferably be tuned to the equation $\Sigma A_{holes} = A_{needle} * F$, where $A_{needle}$ is the cross-sectional area of the needle, and where F is a nonlinearity factor, F>1, related to the losses due to the edge effects at each port such that $1 \le F \le 10$. (F accounts for the nonlinear losses that occur due to fluid molecules bouncing into each other at edges and interfaces.) It is preferable that the device has a sum of areas of its outlet holes that is greater than the area of the needle relevant to the holes. Referring specifically to FIGS. 2D and 2E, in some embodiments, the diameter of the ports will vary to accommodate for the pressure drop along the needle or cannula. In these embodiments, the holes near the distal end of the needle are preferably equal or larger in area than those near the proximal end or hub, such that $A_3 > A_2 > A_1$ where $\Sigma A_i \ge A_{needle} \ge A_1$ is defined as the cross-sectional area of a port, and the definition of $A_3, A_2, A_1$, is the cross-sectional area of individual ports based on the relationship of $A_3 > A_2 > A_1$.

In one embodiment, the burst uses pressures in the range of 1 psi to 200 psi, where the pressure is below that which may cut soft tissue. The saline or other fluid that is delivered during the high-pressure burst is delivered in bolus volumes, preferably ranging from 0.1 mL to 20 mL. An optional stopcock, pinch valve or other control mechanism may be used to separate the high-pressure burst fluid from the standard device fluid. The high-pressure system must be constructed of components that can withstand high pressure without flexing or absorbing pressure to maintain the most efficient transfer of pressure to the jet at the tissue interface. This includes a high-pressure syringe, tubing, stopcock, and any other components helpful in practicing the invention. The components are preferably required to be sterile, and, the components are also preferably disposable and made of any of a variety of plastics. Reusable components may also be used, requiring sterilization prior to use with each patient.

Figure 6A:
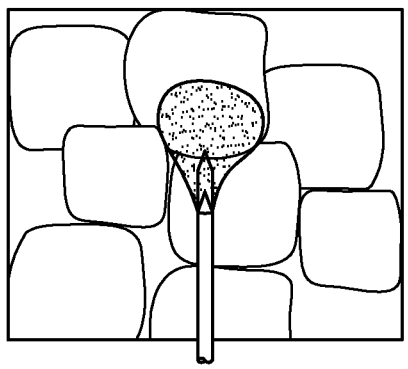
FIGS. 6A and 6B depict the high-pressure burst of the present invention.
Figure 6B:
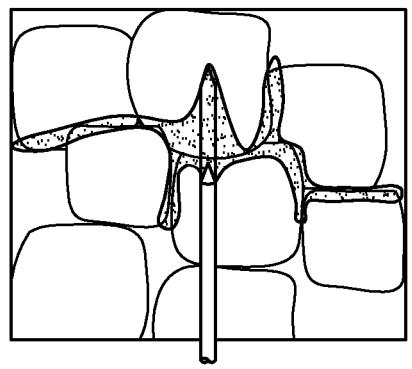

FIG. 6A depicts a scenario in which a solution is delivered into the treatment area via a typical needle configuration. The solution, confined by surrounding tissue and fiber septae, is confined to a limited area, with minimal, if any, diffusion of the solution into adjoining chambers of adipose tissue. In the method of the present invention, a saline solution is pre-injected through needle 200 at a high pressure, after which the standard delivery of fluid is performed. As depicted by FIG. 6B the high pressure burst creates low resistance pathways in the tissue along the walls created by the fibrous structures of the subdermal treatment area and allows subsequent fluid delivery to reach a wider area. In an embodiment including a needle or cannula with multiple ports 204, 308 (FIGS. 2A through 2E, and/or 3A through 3C) the burst is performed along the ports at sufficient pressure to create multiple congruent low-resistance pathways in the treatment area along the fibrous structures therein.

Figure 7A:
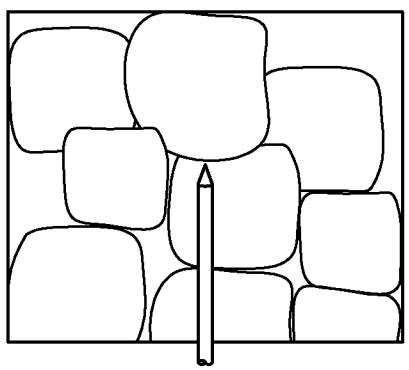
FIGS. 7A-7C depict an embodiment of the high pressure burst.
Figure 7B:
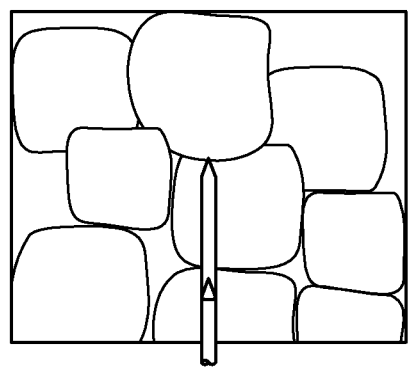
Figure 7C:
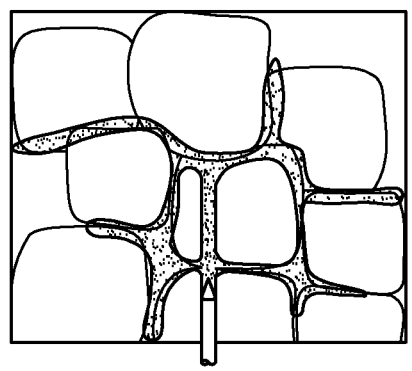

FIGS. 7A through 7C depict a virtual soaker operation whereby the needle is deployed into the treatment area only to be subsequently retracted creating a cavity within the treatment area including disrupted fibrous septae and/or fat cells and/or chambers of fat cells. The pre-injection burst is then performed into the open channel formed from the cavity to achieve a larger network of pathways and an even more extensive distribution of fluid. In one aspect, the needle is deployed in the tissue, a high pressure burst of saline or other inert fluid is injected, followed by a single or series of injections as part of the medical device operation.

In a second aspect, a needle is deployed and then retracted before performing the high pressure burst and low-pressure fluid delivery.

Device 200 is deployed into the soft tissue by percutaneous injection (e.g., FIGS. 1A and 1B). The needle or cannula may be a medical beveled tip, trocar tip, rounded, square or any other needle tip. The needle may optionally require a second needle or introducer to pierce the skin, or the needle may itself pierce the skin. The high-pressure system may be driven by either pneumatic control, hydraulic control, or electrical motor control. The orientation and direction of the water jets may be manually or automatically controlled (e.g., by ports 204, 308). The jets may emanate perpendicularly to the needle, parallel to the needle (from the tip of the needle) or any angle between.

Figure 8A:
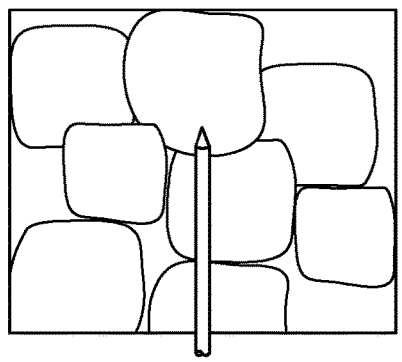
FIGS. 8A-8D depict an embodiment of the high pressure burst.
Figure 8B:
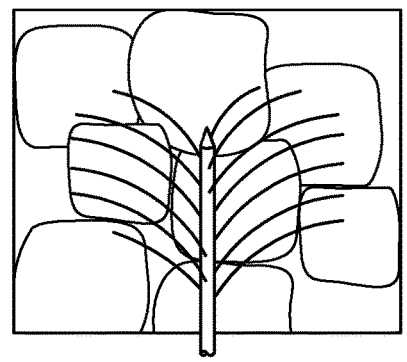
Figure 8C:
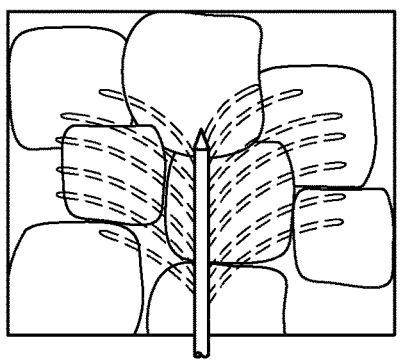
Figure 8D:
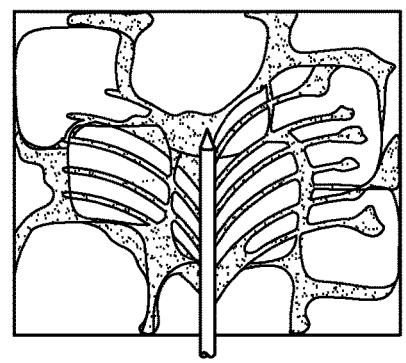

As depicted by FIGS. 8A through 8D, device 200 may be deployed with tines/electrodes 402 to practice the burst of the present invention. As depicted by FIG. 8A, needle 210, 300 is first percutaneously inserted into the treatment area. Once in place, as depicted by FIG. 8B, array 402 of elements 408 are then deployed through ports 308 (e.g., FIG. 3B) such that each element 408 is extended to pierce, disrupt and/or destroy fibrous structures 108 and/or chambers 112 and/or cell groups 114, thereby opening multiple fluid channels through the tissue, fat cells, and fibrous structures in the treatment area. Ports 308 are preferably configured such that when elements 408 are extended outward beyond the circumference of needle 300 elements 408 extend outward in a direction parallel to the surface of the skin 102. This maintains pressure within the treatment area and prevents damage to the outer layer of the dermis during treatment. Elements 408 are subsequently retracted, as depicted by FIG. 8C, to provide for greater permeability of the injected solution to the area. It is not necessary that elements 408 are first removed, so long as the fluid remains pressurized throughout device 200 with pressure at each port 308 being substantially uniform. In one embodiment uniform pressure is achieved by tuning the port diameters consistent with the above equation. In one embodiment incorporating needle 300 including capillaries 302 uniform pressure is achieved by applying a pressurized fluid at junction 304, at an even rate, such that the solution is dispersed evenly by each capillary 302.

Figure 9:
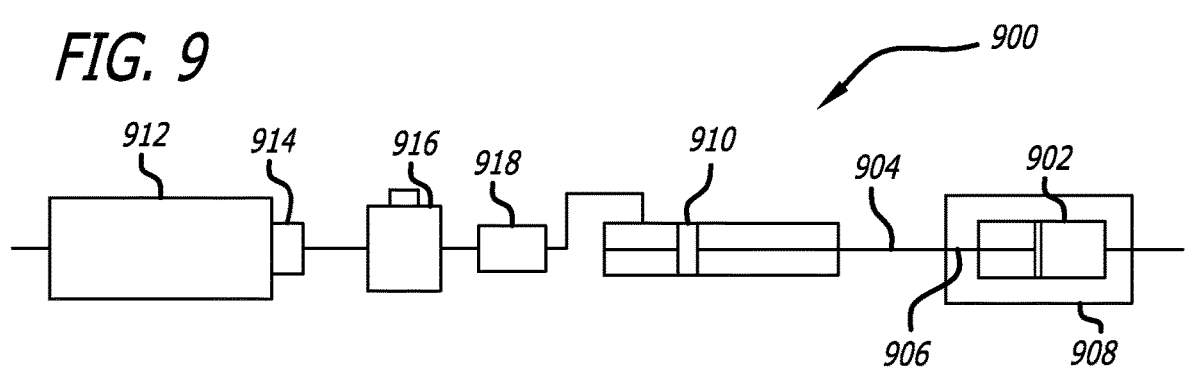
FIG. 9 depicts a high-pressure system configuration.

FIG. 9 depicts device 200 used in conjunction with a pneumatic drive. A pneumatic drive system 900 may be used to practice the above method to provide pressurization and infusion of solution and/or medication into the treatment area. In one exemplary embodiment, a sterile syringe 902 is fastened to a pressurized line 904 at its proximal-driving end 906. The syringe 902 with the high-pressure driver 906 includes a high-pressure system 908. Pressurized line 904 is pressurized by a pneumatic piston 910 which in-turn is driven by a compressor 912. Compressor 912 may be any compressor system known in the art, for instance, but not limited to, air, hydraulic, or $CO_2$ canister. In one embodiment a sensor 914 is disposed at the compressor output to provide for automatic shut-off if the pressure exceeds a predetermined limit. Compressor 912 may further includes a reservoir 916 and a regulator 918 to provide proper delivery of the pneumatic driving force. Reservoir 916 and regulator 918 may be any reservoir and regulator known in the art. The compressor system drives piston 910 to in-turn drive high-pressure system 908 to deliver the high-pressure burst of the present invention.

Figure 10A:
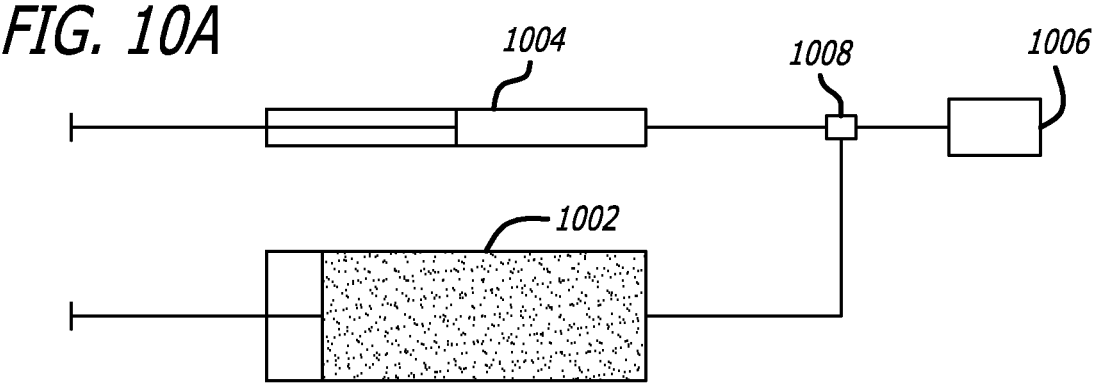
FIGS. 10A-10C depict an aspect of the high-pressure system configuration.
Figure 10B:
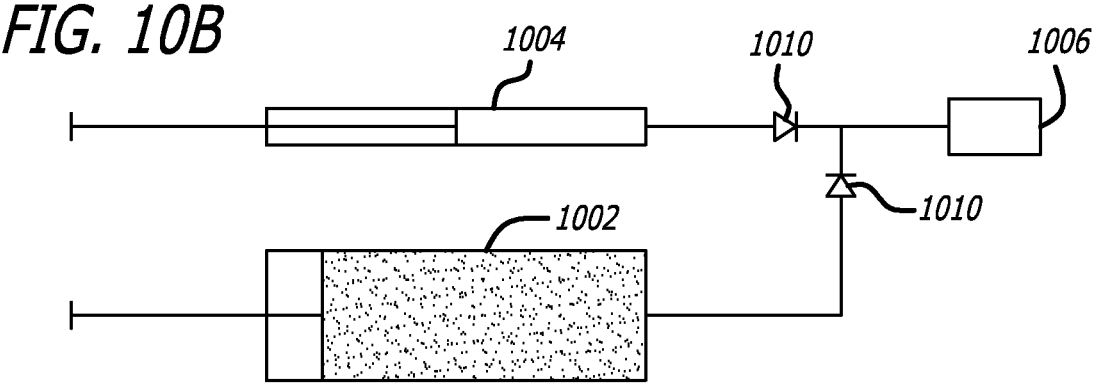
Figure 10C:
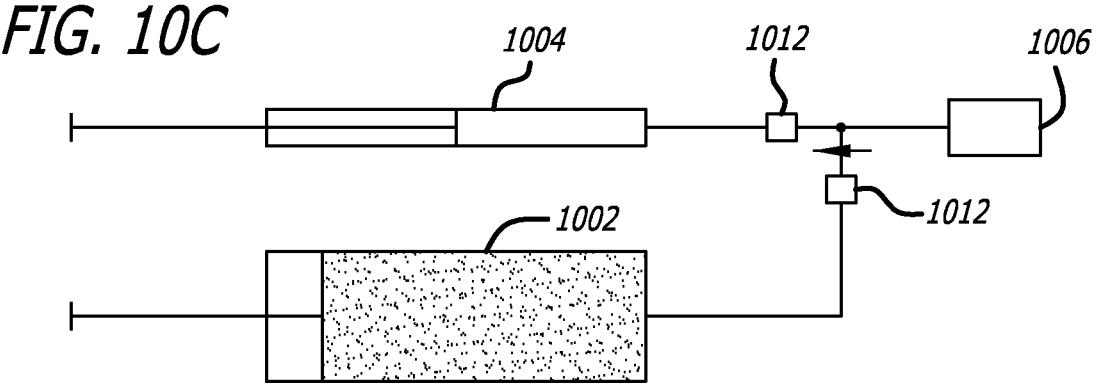

As depicted by FIGS. 10A through 10C, a fluid control device isolates a delivery device 1006 (e.g., needle or other delivery handpiece) from the fluid infusion system 1002 and the high-pressure system 1004. The fluid control device may be a stopcock 1008 (FIG. 10A), one-way valve 1010 (FIG. 10B), pinch valve 1012 (FIG. 10C), or other fluid control device capable of separating the high pressure flow system 1004 from the standard device flow system 1002 in the case that the standard device fluid does not tolerate high pressures or is negatively impacted by a high pressure impulse to the fluid. A stopcock, pinch valve, or other fluid control device such as check valves or one-way valves may be used in conjunction with the syringes 1002 so that after a burst, when the driving piston of the system is retracted, a fresh volume of fluid is drawn into the syringe chamber.

Figure 11A:
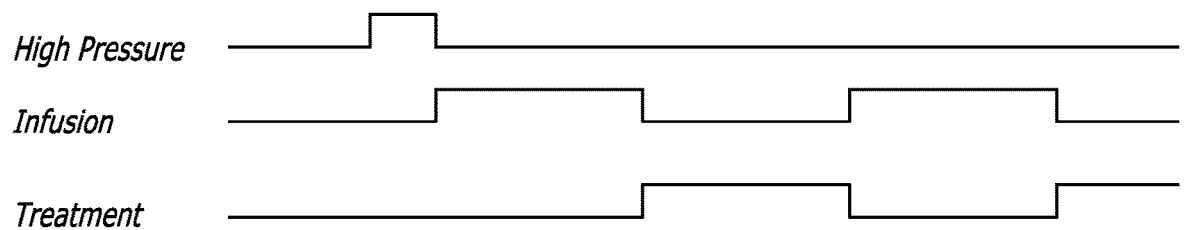
FIGS. 11A and 11B depict the interleaved functions of the invention.
Figure 11B:
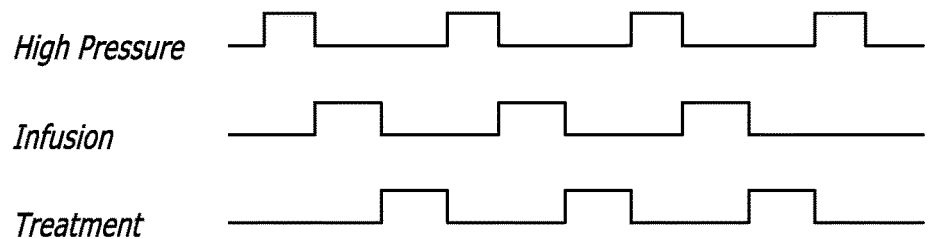

In some embodiments the high-pressure burst will be used in conjunction with infusion of a pre-treatment solution, followed by some other subsequent treatment. The treatment my be the application of an energy source to the pre-treatment solution, or, in some embodiments, may be the application or further infusion of a treatment solution to the treatment area. In either case, the treatment process may be interleaved such that, as depicted by FIGS. 11A and 11B, the steps of infusion and treatment follow the high-pressure burst. The interleaving of the treatment process may be controlled or coordinated by a microprocessor or computer system or may be mechanically or manually interleaved, depending on the condition to be treated and the means available to the treating physician or technician. FIG. 11A depicts the process of interleaving the infusion and treatment whereby a high pressure burst is initiated into the treatment area followed by an immediate infusion into the treatment area. In the preferred embodiment the pressure function is rectangular in shape, with little rise time and fall time so that the maximum pressure is delivered for at all times during the burst. On completion of the infusion (on the fall of the infusion function), the treatment function is initiated, followed by one or more iterations of infusion and treatment. FIG. 11B depicts the process of interleaving the high pressure burst, infusion, and treatment. A high-pressure burst is performed followed by infusion followed by treatment. In one aspect, the steps depicted by FIGS. 11A and/or 11B are repeated one or more times. In the embodiments it is not necessary that each step of burst, infusion, and treatment immediately follow the preceding step. It is possible to program or initiate a delay between selected steps according to a treatment plan.

The forgoing description for the preferred embodiments of the invention has been presented for the purposes of illustration and description. It is not intended to be exhaustive or to limit the invention to the precise form disclosed. Many modifications and variations are possible in light of the above teaching. For example, it is possible to combine the various embodiments, the aspects thereof, and the equivalents thereof to achieve the objective of the present invention. It is intended that the scope of the invention not be limited by this detailed description, but by the claims and the equivalents to the claims appended hereto.

Although the present invention has been described in detail with regard to the preferred embodiments and drawings thereof, it should be apparent to those of ordinary skill in the art that various adaptations and modifications of the present invention may be accomplished without departing from the spirit and the scope of the invention. Accordingly, it is to be understood that the detailed description and the accompanying drawings as set forth hereinabove are not intended to limit the breadth of the present invention.

We claim:

1. A device, comprising:
   a hollow needle having a lumen and a plurality of injection ports comprising at least a first injection port, port $A_1$, a second injection port, port $A_2$, and a third injection port, port $A_3$,
   wherein each of the plurality of injection ports increase in diameter from the proximal to the distal region of the needle, with said port $A_3$ having an area greater than an area of said port $A_2$ and the area of said port $A_2$ being greater than an area of said port $A_1$,
   wherein $\Sigma A_i \geq A_{needle}$, and $A_{needle}$ is the cross-sectional area of the needle and $A_i$ is the cross-sectional area of the plurality of injection ports,
   a plurality of individual channels within the lumen of the needle, the plurality of individual channels being oriented substantially parallel to a central longitudinal axis of the needle, wherein each of the plurality of injection ports is in fluid communication with one of the plurality of individual channels disposed within the lumen of the needle.

2. The device of claim 1, wherein the plurality of injection ports are staggered.

3. The device of claim 1, wherein the plurality of injection ports are linearly disposed along the outer surface of the needle.

4. The device of claim 1, wherein the needle is flexible.

5. The device of claim 1, further comprising:
   a plurality of elongated elements disposed within the needle and capable of movement from a first retracted configuration within the needle through the plurality of injection ports to a second extended configuration outside the needle, wherein the distal ends of the elongated elements are farther apart from each other in the extended configuration than in the retracted configuration.

6. The device of claim 5, wherein the plurality of elongated elements, at least one elongated element is an electrode, and wherein the at least one electrode is at least partially electrically insulated.

7. The device of claim 5 wherein at least one of the plurality of elongated elements is one of a cutting element and a harmonic scalpel.

8. A device, comprising:
   a hollow needle having a lumen and a plurality of injection ports comprising at least a first injection port, port $A_1$, a second injection port, port $A_2$, and a third injection port, port $A_3$,
   wherein said port $A_1$ is positioned in a proximal region of the needle, said port $A_3$ is positioned in a distal region of the needle, said port $A_2$ is positioned between said port $A_1$ and said port $A_3$, each of the plurality of injection ports extending through an outer surface of the needle and in fluid connection with the lumen, and said port $A_3$ is the distal-most port that extends through the outer surface of the needle; and
   wherein each of the plurality of injection ports increase in diameter from the proximal to the distal region of the needle, with said port $A_3$ having an area greater than an area of said port $A_2$ and the area of said port $A_2$ being greater than an area of said port $A_1$,
   wherein $\Sigma A_i \geq A_{needle}$, and $A_{needle}$ is the cross-sectional area of the needle and $A_i$ is the cross-sectional area of the plurality of injection ports;
   a compressor system in fluidic connection with the needle and configured to pressurize a fluid to be delivered to a destination via the plurality of injection ports,
   wherein a placement and cross-sectional area of the plurality of injection ports relative to the needle enables delivery of a volume of the fluid of between 0.1 mL and 20 mL at a pressure between 1 to 200 pounds per square inch and in a plane parallel to a skin surface, when the needle is inserted percutaneously and parallel to the overall surface of the skin, and
   a plurality of individual channels within the lumen of the needle, wherein each of the plurality of injection ports is in fluid communication with a corresponding one of the plurality of channels and wherein the plurality of individual channels are each oriented substantially parallel to a central longitudinal axis of the needle.

9. The device of claim 8, wherein the plurality of injection ports are linearly disposed along the outer surface of the needle.

10. A device, comprising:
    a hollow needle having a lumen and a plurality of injection ports comprising at least a first injection port, port $A_1$, a second injection port, port $A_2$, and a third injection port, port $A_3$,
    wherein said port $A_1$ is positioned in a proximal region of the needle, said port $A_3$ is positioned in a distal region of the needle, said port $A_2$ is positioned between said port $A_1$ and said port $A_3$, each of the plurality of injection ports extending through an outer surface of the needle and in fluid connection with the lumen, and said port $A_3$ is the distal-most port that extends through the outer surface of the needle; and
    wherein each of the plurality of injection ports increase in diameter from the proximal to the distal region of the needle, with said port $A_3$ having an area greater than an area of said port $A_2$ and the area of said port $A_2$ being greater than an area of said port $A_1$,
    wherein $\Sigma A_i \geq A_{needle}$, and $A_{needle}$ is the cross-sectional area of the needle and $A_i$ is the cross-sectional area of the plurality of injection ports; and
    a plurality of individual channels within the lumen of the needle,
    wherein each one of the plurality of individual channels is in fluid communication with a corresponding one of the plurality of injection ports, and
    wherein each one of the plurality of individual channels is oriented substantially parallel to a central longitudinal axis of the needle.

11. The device of claim 10, wherein the plurality of injection ports are linearly disposed along the outer surface of the needle.

12. The device of claim 10, wherein the plurality of individual channels is grouped in an array about the central longitudinal axis of the needle.

13. The device of claim 12, wherein individual channels of the array that are located closer to the central longitudinal axis of the needle terminate at a more distal location along the needle as compared to those individual channels of the array that are located farther from the central longitudinal axis of the needle.

14. The device of claim 10, wherein the plurality of injection ports are aligned along the needle to allow a fluid released from said needle to be released at a specified angle relative to the central longitudinal axis of the needle.

15. The device of claim 10, wherein the needle is flexible.

16. The device of claim 10, further comprising:
    a plurality of elongated elements disposed within the needle and capable of movement from a first retracted configuration within the needle through the plurality of injection ports to a second extended configuration outside the needle, wherein the distal ends of the elongated elements are farther apart from each other in the extended configuration than in the retracted configuration.

\* \* \* \* \*